US005563042A

United States Patent [19]
Phillips et al.

[11] Patent Number: 5,563,042
[45] Date of Patent: * Oct. 8, 1996

[54] WHOLE BLOOD GLUCOSE TEST STRIP

[75] Inventors: Roger Phillips, Palo Alto; Geoffery McGarraugh, Scotts Valley; Franklin A. Jurik, San Mateo; Raymond D. Underwood, Red Bluff, all of Calif.

[73] Assignee: LifeScan, Inc., Milpitas, Calif.

[*] Notice: The term of this patent shall not extend beyond the expiration date of Pat. No. 5,426,032.

[21] Appl. No.: 408,064

[22] Filed: Mar. 21, 1995

Related U.S. Application Data

[60] Continuation of Ser. No. 148,055, Nov. 5, 1993, Pat. No. 5,426,032, which is a division of Ser. No. 6,859, Jan. 21, 1993, abandoned, which is a division of Ser. No. 819,431, Jan. 10, 1992, abandoned, which is a division of Ser. No. 187,602, Apr. 28, 1988, Pat. No. 5,179,005, which is a continuation-in-part of Ser. No. 896,418, Aug. 13, 1986, Pat. No. 4,935,346.

[51] Int. Cl.$^6$ ............... C12Q 1/54; G01N 21/00; G01N 21/77
[52] U.S. Cl. ............... 435/14; 435/805; 435/808; 422/56; 422/58
[58] Field of Search ............... 435/4, 14, 25, 435/28, 805, 808, 968, 970; 422/56, 57, 58

[56] References Cited

U.S. PATENT DOCUMENTS

| | | | |
|---|---|---|---|
| 2,297,248 | 9/1942 | Rudolph | 18/48 |
| 2,893,843 | 7/1959 | Adams | 23/253 |
| 2,893,844 | 7/1959 | Cook. | |
| 3,061,523 | 10/1962 | Free | 195/103.5 |

(List continued on next page.)

FOREIGN PATENT DOCUMENTS

| | | |
|---|---|---|
| 66186/86 | of 0000 | Australia. |
| 4503385 | 1/1986 | Australia. |
| 71187/87 | 1/1988 | Australia. |
| 76758/87 | 2/1988 | Australia. |
| 1117374 | 2/1982 | Canada. |
| 0095057 | 9/1980 | European Pat. Off.. |

(List continued on next page.)

OTHER PUBLICATIONS

Ngo, T., A Sensitive And Versatile Chromogenic Assay For Peroxidase And Peroxidase–Coupled Reactions, Anal Biochem 105 389–397 (1980).

Lo, D. H. et al., "Quantitative Estimate of Total Bilirubin in Serum Using the Kodak Ektachem Clinical Chemistry Slide" (TBIL), Jul. 31, 1984.

(List continued on next page.)

Primary Examiner—Ralph J. Gitomer

[57] ABSTRACT

A whole blood glucose test strip for measuring glucose in an unmeasured whole blood sample which does not require removal of excess sample, and which is adapted for use in a reflectance reading apparatus which measures reflectance at about 635 nm and about 700 nm, the test strip comprising a handle having an aperture defined therein; and a porous, hydrophilic matrix disposed over the aperture such that one surface of the matrix is exposed to the atmosphere adjacent to one side of the strip and the other surface of the matrix is exposed to the atmosphere on the other side of the strip through the aperture, one of the surfaces being an upper sample receiving surface adapted to receive the whole blood sample on one side of the matrix and the second of the surfaces being a lower testing surface from which diffuse reflected light is measurable, the testing surface being opposite to the sample receiving surface. The matrix allows the blood color of the blood sample to be observed from the testing surface, allows at least a portion of the blood sample to penetrate through the matrix from the sample receiving surface to the testing surface, and filters out red blood cells such that they do not reach the testing surface. The matrix comprises reagent means for chemically reacting with glucose to create a change in reflectance which is indicative of the concentration of glucose present in the sample.

25 Claims, 9 Drawing Sheets

U.S. PATENT DOCUMENTS

| Patent # | Date | Inventor | Class |
|---|---|---|---|
| 3,092,465 | 6/1963 | Adams et al. | 23/253 |
| 3,099,605 | 7/1963 | Free | 195/103.5 |
| 3,127,281 | 3/1964 | Meyer | 117/4 |
| 3,232,710 | 2/1966 | Rieckmann et al. | 23/253 |
| 3,298,789 | 1/1967 | Mast | 23/253 |
| 3,413,198 | 11/1968 | Deutsch | 195/103.5 |
| 3,443,903 | 5/1969 | Haack | 23/230 |
| 3,483,031 | 12/1969 | Lauer et al. | 127/41 |
| 3,501,009 | 3/1970 | Jaworek | 210/198 |
| 3,506,126 | 4/1970 | Serfass | 210/96 |
| 3,509,025 | 4/1970 | Bergmeyer et al. | 195/103.5 |
| 3,511,608 | 5/1970 | Anderson | 23/253 |
| 3,552,925 | 1/1971 | Fetter | 23/230 |
| 3,552,928 | 1/1971 | Fetter | 23/253 |
| 3,591,480 | 7/1971 | Neff et al. | 204/195 |
| 3,593,568 | 7/1971 | Schmitz et al. | 73/64.1 |
| 3,607,093 | 9/1971 | Stone | 23/253 |
| 3,620,677 | 11/1971 | Morison | 23/253 |
| 3,630,957 | 12/1971 | Rey et al. | 257/408 |
| 3,650,698 | 3/1972 | Adler | 23/253 |
| 3,653,836 | 4/1972 | Gruber et al. | 23/230 B |
| 3,660,638 | 5/1972 | Oberli | 235/61 |
| 3,663,175 | 5/1972 | Depositar et al. | 23/230 B |
| 3,672,838 | 6/1972 | Trcka et al. | 23/230 |
| 3,677,901 | 7/1972 | Bergmeyer et al. | 195/66 R |
| 3,703,336 | 11/1972 | Rosse et al. | 356/39 |
| 3,713,986 | 1/1973 | Bergmeyer et al. | 195/103.5 R |
| 3,715,192 | 2/1973 | Wenz et al. | 23/253 TP |
| 3,718,439 | 2/1973 | Rosse et al. | 23/259 |
| 3,723,064 | 3/1973 | Liotta | 23/230 R |
| 3,762,609 | 10/1973 | Hagen et al. | 222/194 |
| 3,775,595 | 11/1973 | Rosse et al. | 235/61.6 H |
| 3,778,350 | 12/1973 | Bergmeyer et al. | 195/103.5 C |
| 3,785,772 | 1/1974 | Coggeshall | 23/253 |
| 3,791,933 | 2/1974 | Moyer et al. | 195/127 |
| 3,795,149 | 3/1974 | Gillette et al. | 73/423 A |
| 3,798,004 | 3/1974 | Zerachia et al. | 23/253 TP |
| 3,802,843 | 4/1974 | Kim | 23/259 |
| 3,804,593 | 4/1974 | Smythe et al. | 23/230 R |
| 3,811,840 | 5/1974 | Bauer et al. | 23/253 |
| 3,814,582 | 6/1974 | Rohrbaugh et al. | 23/230 R |
| 3,822,285 | 7/1974 | Werner et al. | 260/315 |
| 3,847,553 | 11/1974 | Verbeck | 23/253 TP |
| 3,853,472 | 12/1974 | Rittersdorf et al. | 23/230 B |
| 3,864,166 | 2/1975 | Barker et al. | 127/46 R |
| 3,876,374 | 4/1975 | Burns | 23/230 R |
| 3,897,214 | 7/1975 | Lange et al. | 23/253 TP |
| 3,901,657 | 8/1975 | Lightfoot | 23/253 TP |
| 3,902,052 | 8/1975 | Amar et al. | 235/151.35 |
| 3,907,503 | 9/1975 | Betts et al. | 23/253 |
| 3,910,701 | 10/1975 | Henderson et al. | 356/39 |
| 3,915,647 | 10/1975 | Wright | 23/253 TP |
| 3,917,452 | 11/1975 | Rittersdorf et al. | 23/230 B |
| 3,917,453 | 11/1975 | Milligan et al. | 23/230 B |
| 3,919,051 | 11/1975 | Koch et al. | 195/103.5 R |
| 3,926,736 | 12/1975 | Bucolo | 195/103.5 R |
| 3,929,581 | 12/1975 | de Fonseca-Wollheim | 195/103.5 R |
| 3,933,593 | 1/1976 | Sternberg | 195/103.5 R |
| 3,936,357 | 2/1976 | Milligan et al. | 195/103.5 R |
| 3,942,995 | 3/1976 | Ichikawa et al. | 106/124 |
| 3,950,133 | 4/1976 | Monte et al. | 23/230 B |
| 3,954,342 | 5/1976 | Boeke | 356/206 |
| 3,957,436 | 5/1976 | Murray | 23/230 R |
| 3,958,560 | 5/1976 | March | |
| 3,960,497 | 6/1976 | Acord | 23/253 R |
| 3,964,870 | 6/1976 | Tiedemann et al. | 23/253 TP |
| 3,971,630 | 7/1976 | Sandrock et al. | 23/230 R |
| 3,973,129 | 8/1976 | Blumberg et al. | 250/461 B |
| 3,975,398 | 8/1976 | Werner et al. | 260/315 |
| 3,979,274 | 9/1976 | Newman | 204/195 |
| 3,980,437 | 9/1976 | Kishimoto et al. | 23/253 TP |
| 3,983,005 | 9/1976 | Goodhue et al. | 195/103.5 R |
| 3,985,508 | 10/1976 | Williams | 23/253 R |
| 3,986,833 | 10/1976 | Mast et al. | 23/230 B |
| 3,988,208 | 10/1976 | Werner et al. | 195/103.5 C |
| 3,990,849 | 11/1976 | Lee et al. | 23/230 |
| 3,992,158 | 11/1976 | Przybylowicz | 422/57 |
| 4,011,046 | 3/1977 | Labes | 23/230 LC |
| 4,015,121 | 3/1977 | Gagnon et al. | 250/221 |
| 4,038,485 | 7/1977 | Johnston et al. | 23/230 B |
| 4,040,786 | 8/1977 | Trivedi et al. | 23/230 R |
| 4,042,335 | 8/1977 | Clement | 23/253 TP |
| 4,043,756 | 8/1977 | Sommervold | 23/230 R |
| 4,050,898 | 9/1977 | Goffe et al. | 23/253 TP |
| 4,056,468 | 11/1977 | Breiter et al. | 210/31 |
| 4,057,394 | 11/1977 | Genshaw | 23/230 |
| 4,059,405 | 11/1977 | Sodickson et al. | 23/230 R |
| 4,061,468 | 12/1977 | Lange et al. | 23/253 TP |
| 4,061,469 | 12/1977 | DuBose | 23/253 R |
| 4,066,403 | 1/1978 | Bruschi | 23/230 B |
| 4,069,017 | 1/1978 | Wu et al. | 23/230 B |
| 4,076,502 | 2/1978 | Dugle et al. | 23/230 R |
| 4,098,574 | 7/1978 | Dappen | 23/230 B |
| 4,110,079 | 8/1978 | Schaeffer et al. | 23/253 TP |
| 4,125,372 | 11/1978 | Kawai et al. | 23/230 |
| 4,135,883 | 1/1979 | McNeil et al. | 422/72 |
| 4,144,306 | 5/1979 | Figueras | 422/56 |
| 4,152,390 | 5/1979 | Nosco et al. | 422/63 |
| 4,153,668 | 5/1979 | Hill et al. | 422/56 |
| 4,160,646 | 7/1979 | Furutani et al. | 23/230 |
| 4,165,508 | 8/1979 | Barter | 340/347 AD |
| 4,176,008 | 11/1979 | Figueras et al. | 435/12 |
| 4,178,153 | 12/1979 | Sodickson | 23/230 |
| 4,180,060 | 12/1979 | Kutter | 128/760 |
| 4,199,260 | 4/1980 | Kusnetz et al. | 356/411 |
| 4,199,261 | 4/1980 | Tidd et al. | 356/448 |
| 4,211,845 | 7/1980 | Genshaw | 435/14 |
| 4,211,845 | 7/1980 | Genshaw et al. | 435/14 |
| 4,219,529 | 8/1980 | Tersteeg et al. | 422/65 |
| 4,224,032 | 9/1980 | Glover et al. | 23/230 B |
| 4,226,537 | 10/1980 | Colley | 356/427 |
| 4,230,456 | 10/1980 | Wu | 23/230 B |
| 4,233,029 | 11/1980 | Columbus | 23/230 R |
| 4,238,196 | 12/1980 | Acuff et al. | 23/230 |
| 4,240,912 | 12/1980 | Stumpf et al. | 210/321.2 |
| 4,253,846 | 3/1981 | Smythe et al. | 23/230 R |
| 4,254,083 | 3/1981 | Columbus | 422/55 |
| 4,255,384 | 3/1981 | Kitajima et al. | 422/57 |
| 4,256,693 | 3/1981 | Kondo et al. | 422/56 |
| 4,257,862 | 3/1981 | Schnipelsky et al. | 204/195 R |
| 4,258,001 | 3/1981 | Pierce et al. | 422/56 |
| 4,261,041 | 4/1981 | Starr | 364/571 |
| 4,269,938 | 5/1981 | Frank | 435/7 |
| 4,272,482 | 6/1981 | Jessop et al. | 422/65 |
| 4,274,832 | 6/1981 | Wu et al. | 23/230 R |
| 4,277,561 | 7/1981 | Monget et al. | 435/14 |
| 4,278,439 | 7/1981 | White | 23/230 B |
| 4,281,062 | 7/1981 | Kallis | 435/14 |
| 4,283,383 | 8/1981 | Masson et al. | 424/12 |
| 4,283,491 | 8/1981 | Dappen | 435/10 |
| 4,288,228 | 9/1981 | Oberhardt | 23/230 |
| 4,292,272 | 9/1981 | Kitajima et al. | 422/57 |
| 4,297,238 | 10/1981 | Vormbrock et al. | 252/408 |
| 4,298,345 | 11/1981 | Sodickson et al. | 23/230 R |
| 4,298,688 | 11/1981 | Kallies | 435/14 |
| 4,299,916 | 11/1981 | Litman et al. | 435/6 |
| 4,300,906 | 11/1981 | Negersmith | 23/230 A |
| 4,302,420 | 11/1981 | Jakubowicz et al. | 422/63 |
| 4,303,406 | 12/1981 | Ross | 8/158 |
| 4,303,408 | 12/1981 | Kim et al. | 23/230 B |
| 4,303,753 | 12/1981 | Lam | 435/14 |
| 4,308,485 | 12/1981 | Ignazio | 313/407 |

| Patent | Date | Name | Class |
|---|---|---|---|
| 4,310,399 | 1/1982 | Columbus | 204/195 R |
| 4,312,834 | 1/1982 | Vogel et al. | 422/56 |
| 4,318,984 | 3/1982 | Magers et al. | 435/14 |
| 4,318,985 | 3/1982 | Bauer et al. | 435/14 |
| 4,325,910 | 4/1982 | Jordan | 422/64 |
| 4,330,299 | 5/1982 | Cerami | 23/230 B |
| 4,336,330 | 6/1982 | Bauer | 435/14 |
| 4,337,065 | 6/1982 | Hiratsuka et al. | 23/230 B |
| 4,340,669 | 7/1982 | Bauer | 435/14 |
| 4,353,983 | 10/1982 | Siddiqi | 435/11 |
| 4,361,648 | 11/1982 | Shuenn-tzong | 435/10 |
| 4,363,874 | 12/1982 | Greenquist | 435/7 |
| 4,366,061 | 12/1982 | Papanek et al. | 210/647 |
| 4,366,241 | 12/1982 | Tom et al. | 435/7 |
| 4,370,983 | 2/1983 | Lichtenstein | 128/630 |
| 4,373,818 | 2/1983 | Yamamoto et al. | 356/408 |
| 4,384,042 | 5/1983 | Milke et al. | 435/25 |
| 4,390,343 | 6/1983 | Walter | 436/518 |
| 4,390,621 | 6/1983 | Bauer | 435/14 |
| 4,391,905 | 7/1983 | Bauer | 435/14 |
| 4,391,906 | 7/1983 | Bauer | 435/14 |
| 4,403,984 | 9/1983 | Ash et al. | 604/50 |
| 4,415,700 | 11/1983 | Betz et al. | 524/548 |
| 4,418,037 | 11/1983 | Katsuyama et al. | 422/56 |
| 4,420,564 | 12/1983 | Tsuji et al. | 435/288 |
| 4,420,566 | 12/1983 | Jessop et al. | 436/46 |
| 4,427,632 | 1/1984 | Okaniwa et al. | 422/56 |
| 4,427,889 | 1/1984 | Müller | 250/339 |
| 4,430,427 | 2/1984 | Hopkins | 435/25 |
| 4,430,436 | 2/1984 | Koyama et al. | 436/531 |
| 4,448,207 | 5/1984 | Parrish | 128/771 |
| 4,449,538 | 5/1984 | Corbitt et al. | 128/760 |
| 4,450,153 | 5/1984 | Hopkins | 424/94 |
| 4,452,887 | 6/1984 | Kitajima et al. | 435/14 |
| 4,458,539 | 7/1984 | Bilstad et al. | 73/861 |
| 4,459,358 | 7/1984 | Berke | 436/170 |
| 4,460,684 | 7/1984 | Bauer | 435/14 |
| 4,464,172 | 8/1984 | Lichtenstein | 604/65 |
| 4,472,498 | 9/1984 | Masuda et al. | 435/7 |
| 4,476,222 | 10/1984 | Ohtani et al. | 435/14 |
| 4,477,575 | 10/1984 | Vogel et al. | 436/170 |
| 4,478,942 | 10/1984 | Katsuyama et al. | 436/66 |
| 4,483,924 | 11/1984 | Tsuji et al. | 435/288 |
| 4,503,555 | 3/1985 | Brimhall, Jr. et al. | 382/6 |
| 4,509,859 | 4/1985 | Markart et al. | 356/446 |
| 4,528,159 | 7/1985 | Liston | 422/65 |
| 4,532,107 | 7/1985 | Siddigi | 422/56 |
| 4,534,012 | 8/1985 | Yokozawa | 364/900 |
| 4,540,670 | 9/1985 | Arai et al. | 436/170 |
| 4,547,460 | 10/1985 | Eikenberry | 435/15 |
| 4,551,307 | 11/1985 | Koyama et al. | 422/56 |
| 4,552,458 | 11/1985 | Lowne | 356/446 |
| 4,553,848 | 11/1985 | Rosicke et al. | 356/448 |
| 4,554,132 | 11/1985 | Collins | 422/68 |
| 4,557,901 | 12/1985 | Koyama et al. | 422/56 |
| 4,562,148 | 12/1985 | Sommer | 435/7 |
| 4,567,024 | 1/1986 | Koyama et al. | 422/56 |
| 4,576,793 | 3/1986 | Koyama et al. | 422/56 |
| 4,578,245 | 3/1986 | Arai et al. | 422/56 |
| 4,587,100 | 5/1986 | Amano et al. | 422/56 |
| 4,587,220 | 5/1986 | Mayambala-Mwanika et al. | 436/66 |
| 4,592,365 | 6/1986 | Georgi | 128/680 |
| 4,592,893 | 6/1986 | Poppe et al. | 422/56 |
| 4,594,224 | 6/1986 | Okaniwa et al. | 422/56 |
| 4,594,327 | 6/1986 | Zuk | 436/514 |
| 4,595,562 | 6/1986 | Liston et al. | 422/65 |
| 4,603,428 | 7/1986 | Sandrik et al. | 378/174 |
| 4,604,254 | 8/1986 | Yamamoto et al. | 264/254 |
| 4,604,264 | 8/1986 | Rothe et al. | 422/56 |
| 4,604,579 | 8/1986 | Cannon et al. | 324/309 |
| 4,618,475 | 10/1986 | Wang | 422/56 |
| 4,622,207 | 11/1986 | Wang | 422/56 |
| 4,627,014 | 12/1986 | Lo et al. | 364/571 |
| 4,627,445 | 12/1986 | Garcia et al. | 128/770 |
| 4,637,403 | 1/1987 | Garcia et al. | 128/770 |
| 4,637,978 | 1/1987 | Dappen | 435/11 |
| 4,642,286 | 2/1987 | Moldowan | 435/25 |
| 4,647,432 | 3/1987 | Wakatake | 422/64 |
| 4,649,123 | 3/1987 | Charlton et al. | 436/79 |
| 4,661,319 | 4/1987 | Lape | 422/68 |
| 4,668,619 | 5/1987 | Greenquist et al. | 435/7 |
| 4,669,878 | 6/1987 | Meier | 356/319 |
| 4,670,218 | 6/1987 | Gantzer et al. | 422/56 |
| 4,671,937 | 6/1987 | Katsuyama et al. | 422/56 |
| 4,685,059 | 8/1987 | Yamamoto | 364/415 |
| 4,686,479 | 8/1987 | Young et al. | 324/439 |
| 4,693,985 | 9/1987 | Degen et al. | 436/531 |
| 4,710,458 | 12/1987 | Maines | 435/12 |
| 4,714,341 | 12/1987 | Hamaguri et al. | 356/41 |
| 4,717,546 | 1/1988 | Barnett | 422/63 |
| 4,731,726 | 3/1988 | Allen, III | 364/416 |
| 4,732,736 | 3/1988 | Kobayashi et al. | 422/56 |
| 4,734,360 | 3/1988 | Phillips | 435/25 |
| 4,748,114 | 5/1988 | Kallies | 435/14 |
| 4,772,561 | 9/1988 | Genshaw | 436/169 |
| 4,773,097 | 9/1988 | Suzaki et al. | 382/6 |
| 4,774,192 | 9/1988 | Terminiello et al. | 436/530 |
| 4,775,637 | 10/1988 | Sutherland et al. | 436/527 |
| 4,780,283 | 10/1988 | Meinecke et al. | 422/68 |
| 4,787,398 | 11/1988 | Garcia et al. | 128/770 |
| 4,790,979 | 12/1988 | Terminiello et al. | 422/56 |
| 4,791,461 | 12/1988 | Kishimoto et al. | 356/446 |
| 4,803,153 | 2/1989 | Shibata et al. | 435/2 |
| 4,803,159 | 2/1989 | Smith-Lewis | 435/26 |
| 4,803,625 | 2/1989 | Fu et al. | 364/413.03 |
| 4,810,470 | 3/1989 | Burkhardt et al. | 422/56 |
| 4,814,142 | 3/1989 | Gleisner | 422/56 |
| 4,816,224 | 3/1989 | Vogel et al. | 422/55 |
| 4,818,710 | 4/1989 | Sutherland et al. | 436/527 |
| 4,820,489 | 4/1989 | Rothe et al. | 422/56 |
| 4,820,649 | 4/1989 | Kawaguchi et al. | 436/501 |
| 4,824,639 | 4/1989 | Hildenbrand et al. | 422/56 |
| 4,839,297 | 6/1989 | Freitag et al. | 436/170 |
| 4,855,108 | 8/1989 | Masuda et al. | 422/56 |
| 4,857,273 | 8/1989 | Stewart | 422/68 |
| 4,870,005 | 9/1989 | Akiyoshi et al. | 435/7 |
| 4,876,204 | 10/1989 | Inoue et al. | 436/46 |
| 4,876,207 | 10/1989 | Mack, II et al. | 436/135 |
| 4,877,747 | 10/1989 | Stewart | 436/525 |
| 4,889,815 | 12/1989 | Bradwell et al. | 436/517 |
| 4,895,704 | 1/1990 | Arai et al. | 422/57 |
| 4,900,666 | 2/1990 | Phillips | 435/25 |
| 4,913,150 | 4/1990 | Cheung et al. | 128/633 |
| 4,914,020 | 4/1990 | Arai et al. | 435/4 |
| 4,929,561 | 5/1990 | Hirschfeld | 436/116 |
| 4,931,384 | 6/1990 | Layton et al. | 435/7 |
| 4,935,346 | 6/1990 | Phillips | 435/14 |
| 4,937,050 | 6/1990 | Meinecke et al. | 422/68.1 |
| 4,943,522 | 7/1990 | Eisinger et al. | 435/7 |
| 4,950,454 | 8/1990 | Masuda et al. | 422/56 |
| 4,952,515 | 8/1990 | Gleisner | 436/169 |
| 4,962,021 | 10/1990 | Meserol et al. | 435/7 |
| 4,965,047 | 10/1990 | Hammond | 422/58 |
| 4,976,724 | 12/1990 | Nieto et al. | 606/182 |
| 4,985,205 | 1/1991 | Fritsche et al. | 422/56 |
| 4,987,085 | 1/1991 | Allen et al. | 436/169 |
| 5,004,584 | 4/1991 | Rayman | 422/58 |
| 5,023,052 | 6/1991 | Nagatomo et al. | 422/56 |
| 5,023,053 | 6/1991 | Finlan | 422/82.05 |
| 5,035,863 | 7/1991 | Finlan et al. | 422/82.05 |
| 5,037,614 | 8/1991 | Makita et al. | 422/68.1 |
| 5,043,269 | 8/1991 | Theodoropulos | 435/28 |
| 5,047,206 | 9/1991 | Dombrowski | 422/56 |
| 5,047,213 | 9/1991 | Finlan et al. | 422/82.11 |

| | | | |
|---|---|---|---|
| 5,047,351 | 9/1991 | Makiuchi et al. | 436/169 |
| 5,049,487 | 9/1991 | Phillips et al. | 435/4 |
| 5,055,265 | 10/1991 | Finlan | 422/82.05 |
| 5,059,394 | 10/1991 | Phillips et al. | 422/68.1 |
| 5,064,619 | 11/1991 | Finlan | 422/82.05 |
| 5,067,093 | 11/1991 | Przybylowicz et al. | 364/498 |
| 5,071,746 | 12/1991 | Wilk et al. | 435/7.94 |
| 5,079,174 | 1/1992 | Buck et al. | 436/538 |
| 5,082,626 | 1/1992 | Grage, Jr. | 422/56 |
| 5,096,809 | 3/1992 | Chen et al. | 435/7.9 |
| 5,096,836 | 3/1992 | Macho et al. | 436/169 |
| 5,104,619 | 4/1992 | deCastro et al. | 422/56 |
| 5,104,793 | 4/1992 | Buck | 435/7.92 |
| 5,104,811 | 4/1992 | Berger et al. | 436/164 |
| 5,106,758 | 4/1992 | Adler et al. | 436/165 |
| 5,110,550 | 5/1992 | Schlipfenbacher et al. | 422/56 |
| 5,110,724 | 5/1992 | Hewett | 435/11 |
| 5,114,350 | 5/1992 | Hewett | 435/288 |
| 5,114,673 | 5/1992 | Berger et al. | 422/56 |
| 5,116,763 | 5/1992 | Greene et al. | 436/95 |
| 5,120,507 | 6/1992 | Sano et al. | 422/82.05 |
| 5,124,128 | 6/1992 | Hildenbrand et al. | 422/56 |
| 5,128,171 | 7/1992 | Gleisner | 427/2 |
| 5,130,231 | 7/1992 | Kennedy et al. | 435/4 |
| 5,130,258 | 7/1992 | Makino et al. | 436/169 |
| 5,147,606 | 9/1992 | Charlton et al. | 422/56 |
| 5,149,505 | 9/1992 | English et al. | 422/99 |
| 5,152,962 | 10/1992 | Lackie | 422/681 |
| 5,166,051 | 11/1992 | Killeen et al. | 435/7.1 |
| 5,171,688 | 12/1992 | Hewett et al. | 435/289 |
| 5,173,261 | 12/1992 | Krause et al. | 422/58 |
| 5,174,963 | 12/1992 | Fuller et al. | 422/82.05 |
| 5,179,005 | 1/1993 | Phillips | 435/14 |
| 5,183,741 | 2/1993 | Arai et al. | 435/14 |
| 5,187,100 | 2/1993 | Matzinger et al. | 436/16 |
| 5,188,966 | 2/1993 | Eikmeier et al. | 436/170 |
| 5,206,177 | 4/1993 | DeLaCroix et al. | 436/518 |
| 5,211,914 | 5/1993 | Vogel et al. | 422/56 |
| 5,212,060 | 5/1993 | Maddox | 435/7.1 |
| 5,215,716 | 6/1993 | Arai | 422/56 |
| 5,217,691 | 6/1993 | Greene et al. | 422/56 |
| 5,227,310 | 7/1993 | Sakamoto et al. | 436/169 |
| 5,252,293 | 10/1993 | Drbal et al. | 422/101 |
| 5,304,468 | 4/1994 | Phillips et al. | 435/14 |

FOREIGN PATENT DOCUMENTS

| | | |
|---|---|---|
| 112166 | 6/1984 | European Pat. Off. |
| 0100173A1 | 6/1984 | European Pat. Off. |
| 0110173 | 6/1984 | European Pat. Off. |
| 0141648A2 | 10/1984 | European Pat. Off. |
| 0166878A2 | 4/1985 | European Pat. Off. |
| 0140337 | 5/1985 | European Pat. Off. |
| 0140337A2 | 5/1985 | European Pat. Off. |
| 0159727A2 | 10/1985 | European Pat. Off. |
| 0169055 | 1/1986 | European Pat. Off. |
| 0173500A1 | 3/1986 | European Pat. Off. |
| 182647 | 5/1986 | European Pat. Off. |
| 183524 | 6/1986 | European Pat. Off. |
| 0295526A1 | 6/1988 | European Pat. Off. |
| 0336483A1 | 3/1989 | European Pat. Off. |
| 0345781A2 | 6/1989 | European Pat. Off. |
| 56-164941 | 12/1981 | Japan. |
| 57-101760 | 6/1982 | Japan. |
| 59-108942 | 6/1984 | Japan. |
| 911181 | 11/1962 | United Kingdom. |
| 1037155 | 7/1966 | United Kingdom. |
| 2026160 | 6/1980 | United Kingdom. |
| 2029012 | 6/1980 | United Kingdom. |
| 2039035 | 7/1980 | United Kingdom. |
| 2090659 | 7/1982 | United Kingdom. |
| 81/00622 | 3/1981 | WIPO. |
| PCT/US82/ 00170 | 8/1982 | WIPO. |
| WO83/00931 | 3/1983 | WIPO. |

OTHER PUBLICATIONS

Tietz, Norbert, et al., Fundamentals of Clinical Chemistry, 1976, pp. 242–243.

Wing, R. R., et al., "Behavioral Skills in Self–Monitoring of Blood Glucose: Relationship to Accuracy" Diabetes Care, vol. 9, No. 4, Jul., Aug. 1986, pp. 330–333.

Clements, R. S. et al., "An Evaluation of Patient Performance of and Their Satisfaction with Various Rapid Blood Glucose Measurement Systems", Diabetes Care, vol. 6, No. 1, Jan.–Feb. 1981, pp. 45–49.

Kodak Ektachem Clinical Chemistry Products (Bates numbered 100572–574) 1981.

"Clinical Analysis Moves into the Doctor's Office", (Bates numbered 100575–576) Jan. 1985.

Ektachem DT60 Analyzer, Robert J. Elliott, *Physicians & Computers* vol. 2, No. 6, Oct. 1984 (Bates numbered 100577–100580).

New Kodak Ektachem DT60 Analyzer, brochure (Bates numbered 100581–100586) 1984.

Kodak announces the analyzer that measures up to its potentiao, brochure (Bates numbered 100587–592) 1980.

Kodak Ektachem DT System, Quality Clinical Diagnostic Products for the Small Laboratory, brochure (Bates numbered 100593–100596) 1987.

Kodak puts colorimetry in a technology by itself, brochure (Bates numbered 100597–602) 1980.

"Development of a Layered–Coating Technology for Clinical Chemistry", T. L. Shirey, *Clinical Biochemistry*, vol. 16, No. 2, pp. 147–155, 1983.

Kodak Ektachem DT Slides—Methodology, Publication No. C–300 (1985) (Bates numbered 100613–618).

Kodak Ektachem DT System brochure (Bates numbered 100619–620) 1986.

Kodak Ektachem DT60 Analyzer—Dry chemistry slides use proven layer–coated technology, brochure (Bates numbered 100621–625) Oct. 1984.

Adlercreutz, H., et al., "Evaluation of the New 'System Olli 3000' Kinetic Ultraviolet Analyzer for Measuring Aspartate and Alanine Aminotransferase and Lactate Dehydrogenase Activities in Serum," *Clinical Chemistry*, vol. 21, No. 6, pp. 676–684 (1975).

Al–Kaissi, E. et al., "Assessment of Substrates for Horseradish Peroxidase in Enzyme Immunoassay," *Journal of Immunological Methods*, 58, pp. 127–132 (1983).

Beckman Enzyme Activity Analyzer, System TR, p. 205.

"Benefits of Self Monitoring of Blood Glucose," *British Medical Journal*, vol. 286, pp. 1230–1231, Apr. 16, 1983.

Blood Glucose Monitors In Health Devices, vol. 17, No. 9, pp. 253–270 (Sep. 1988).

Capaldi, Dante J. et al., "A New Peroxidase Color Reaction: Oxidative Coupling of 3–Methyl–2–Benzothiazolinone Hydrazone (MBTH) with its Formaldehyde Azine, Application to Glucose and Choline Oxidases," *Analytical Biochemistry*, 129, 329–336 (1983).

Carrick, C. E., "Barriers to Performance of Maintenance and Quality Control (QC) by Patients Using Home Glucose Meters," *Diabetes*, May 1990, vol. 39, Supp. 1, The Program for the 50th Annual Meeting of the American Diabetes Association in Atlanta, Georgia, Abstract #205.

Cate, J. C. IV, "Evaluation of an Engineering Model of the 'Ektachem' Analyzer for Glucose and Urea Assay," *Clinical Chemistry*, vol. 26, No. 2, p. 266 (1980).

Chua, K. S., et al., "Plasma Glucose Measurement with the Yellow Springs Glucose Analyzer," *Clinical Chemistry*, vol. 24, No. 1, pp. 150–152 (1978).

Coagulation Analyzer, Model CA550 (Bio–Dynamics, Inc.), p. 167 No Date Avail.

Cohen, Matthew et al., "Self–Monitoring of Blood Glucose Levels in Non–Insulin–Dependent Diabetes Mellitus," *The Medical Journal of Australia*, pp. 377–380, Oct. 15, 1983.

Cohen, Mathew et al., "Home Blood–Glucose Monitoring—A New approach to the Management of Diabetes Mellitus," *The Medical Journal of Australia*, pp. 713–716, Dec. 27, 1980.

Cowles, John C., "Theory of Dual–Wavelength Spectrophotometry for Turbid Samples," *Journal of the Optical Society of America*, vol. 55, No. 6, pp. 690–693, Jun. 1965.

Curme, H. G., et al., "Multilayer Film Elements for Clinical Analysis: General Concepts," *Clinical Chemistry*, vol. 24, No. 8, pp. 1335–1342 (1978).

Davidson, J. A., et al., "Evaluation of a New Blood Glucose Meter and Test Strip Intended for Hospital Bedside Glucose Testing," *Diabetes*, May 1990, vol. 39, Supp. 1, The Program for the 50th Annual Meeting of the American Diabetes Association in Atlanta, Georgia, Abstract #871.

Driscoll, R. C., et al., "Discrete Automated Chemistry System with Tableted Reagents," *Clinical Chemistry*, vol. 29, No. 9, p. 1609 (1983).

Ervin, K. R., et al., "New Enzymatic Test Strip For Alcohol In Saliva: Its Utility In Roadside and Consumer Use" (Mar. 1986).

Evenson, M. S., et al., "Peak Characteristics and Computers in Continuous Flow Analysis," *Clinical Chemistry*, vol. 16, No. 7, pp. 606–611 (1970).

Fairclough et al., "An Evaluation Of Patient Performance Of and Their Satisfaction With Various Rapid Blood Glucose Measurement Systems," *Diabetes Care*, vol. 6, No. 1, pp. 45–49 (1981).

Feldman, Jerome M. et al., "Ihibition of Glucose Oxidase Paper Tests by Reducing Metabolites," *Diabetes*, vol. 19, No. 5, pp. 337–343 (May, 1970).

Fleming, D. R., "Who Benefits from Automatic Record Keeping," *Diabetes*, May 1990, vol. 39, Supp. 1, The Program for the 50th Annual Meeting of the American Diabetes Association in Atlanta, Georgia, Abstract #862.

Funnell, M. M., et al., "Perceived Effectiveness, Cost and Availability of Patient Education Methods and Materials," *Diabetes*, May 1990, vol. 39, Supp. 1, The Program for the 50th Annual Meeting of the American Diabetes Association in Atlanta, Georgia, Abstract #200.

Geoghegan, William D. et al., "Adaptation of the Ngo–Lenhoff Peroxidase Assay for Solid Phase Elisa," *Journal of Immunological Methods*, 60, pp. 61–68 (1983).

Geoghegan in Enzyme–Mediated Immunoassay, edited by Ngo and Lenhoff (1985) pp. 451–465.

Gilden, J. L., et al., "Matchmaker: A Visual Reader Improves Monitoring Accuracy, Quality of Life and Glycemic Control in Elderly Diabetics," *Diabetes*, May 1990, vol. 39, Supp. 1, The Program for the 50th Annual Meeting of the American Diabetes Association in Atlanta, Georgia, Abstract #868.

Hahn B., et al., "Polychromatic Analysis: New Applications of an Old Technique," *Clin. Chem.*, 25/6, pp. 951–959 (1979).

Hardin, E., et al., "Clinical Laboratory Evaluation of the Perkin–Elmer KA–150 Enzyme Analyzer," *Clinical Chemistry*, vol. 22, No. 4, pp. 434, 437 (1976).

Havlin, C. E., et al., "Critical Evaluation of Blood Glucose Monitoring Devices," *Diabetes*, May 1990, vol. 39, Supp. 1, The Program for the 50th Annual Meeting of the American Diabetes Association in Atlanta, Georgia, Abstract #873.

Ikeda, Y. et al., "Pilot Study of Self–Measurement of Blood Glucose Using the Dextrostix–Eyetone System for Juveniel–Onset Diabetes," *Diabetologia*, 15, pp. 91–93 (1978).

Jarrett, L., et al., "Home Blood Glucose Meters with Memories," *Diabetes*, May 1990, vol. 39, Supp. 1, The Program for the 50th Annual Meeting of the American Diabetes Association in Atlanta, Georgia, Abstract #685.

Keilin, D., "Properties of Glucose Oxidase (Notatin)," *Biochem.*, 42, pp. 221–229 (1948).

Kessler, G. et al., "Bichromatic Analysis as Applied to the Technicon STAC Biochemical Analyzer," pp. 28–35 No date avail.

Kineiko, R. W., et al., "Laboratory Evaluation of the Boehringer Mannheim 'Hitachi 705' Automatic Analyzer," *Clinical Chemistry*, vol. 29, No. 4, p. 688 (1983).

Lee, E. Y., et al., "Do Physicians Appropriately Utilize Inpatient Bedside Glucose Monitoring?," *Diabetes*, May 1990, vol. 39, Supp. 1, The Program for the 50th Annual Meeting of the American Diabetes Association in Atlanta, Georgia, Abstract #883.

Leroux et al., "Ward Level Evaluation Of The 'One Touch' Glucose Meter," *Clin. Chem.*, vol. 34 No. 9, 1988, p. 1928.

Lifescan, Inc., Alcoscan Technical Paper, "Alcoscan Reagent Chemistry," Mar. 1985.

Lifescan, Inc., Alcoscan Technical Papers, "The Correlation Between Blood and Saliva Alcohol Concentrations—An Historical Perspective;" Driving Under the Influence San Francisco Bay Area Holiday Experiment; Correlation of Alcoscan System and Head Space Gas Chromatography; Storage of Reacted Alcoscan Test Strips, Mar. 1985.

"Materials and Methods," *Clinical Chemistry*, vol. 24, No. 12, p. 2126 (1978).

Morgenstern, Stan et al., "STAC Rate Reaction and Fixed–Point Methods," pp. 16–22, Dec. 1976.

Morris, D. L. et al., "A Chemistry for the Immobilization of Enzymes on Nylon," *Biochem. J.*, vol. 147(3), pp. 593–603 (1975).

Murkin, S. A., et al., "Anchored Instruction (AI) Enhances Diabetes (DM) Problem Solving," *Diabetes*, May 1990, vol. 39, Supp. 1, The Program for the 50th Annual Meeting of the American Diabetes Association in Atlanta, Georgia, Abstract #65.

Ngo, T. T., et al., "A Sensitive and Versatile Chromogenic Assay for Peroxidase and Peroxidase–Coupled Reactions," *Analytical Biochemistry*, 105, pp. 389–397 (1980).

Ohkubo et al., "Plasma Glucose Concentrations Of Whole Blood, As Determined With A Multilayer–Film Analytical Element," *Clinical Chemistry*, vol. 27, No. 7, (1981) pp. 1287–1290.

Passey, R., et al., "Evaluation of the Beckman 'System TR Enzyme Analyzer'," *Clinical Chemistry*, vol. 21, No. 8, pp. 1107–1112 (1975).

Pellegrino, L. S., et al., "Pilot study: Blood Glucose Monitors," *Diabetes*, May 1990, vol. 39, Supp. 1, The Program for the 50th Annual Meeting of the American Diabetes Association in Atlanta, Georgia, Abstract #882.

Percy–Robb, I. W., et al., "The Peak Monitor of the Technicon SMAC System," *Clinical Chemisty*, vol. 24, No. 1, pp. 146–148 (1978).

Powers et al., "Quantitative Estimate Of Total Bilirubin In Serum Using The Kodak Ektachem Clinical Chemistryl Slide (TBIL)," 1984.

Rachlin, J. A., et al., "User Errors in Blood Glucose Monitoring," *Diabetes*, May 1990, vol. 39, Supp. 1, The Program for the 50th Annual Meeting of the American Diabetes Association in Atlanta, Georgia, Abstract #879.

Ratzlaff, K. L. et al., "Theoretical Assessment of Precision in Dual Wavelength Spectrophotometric Measurement," *Analytical Chemistry*, vol. 49, No. 14, pp. 2170–2176, Dec. 1977.

Richards, F. M. et al., "Glutaraldehyde as a Protein Cross–linking Reagent," *J. Mol. Biol.*, 37, pp. 231–233 (1968).

Rikmenspoel, Robert, "The Sensitivity and Accuracy of Dual–Wavelength Spectrophotometers," *Applied Optics*, vol. 3, No. 3, pp. 351–355, Mar. 1964.

Schocken, D. M., et al., "Marketing Diabetes Education Reaches Primary Care Physicians," *Diabetes*, May 1990, vol. 39, Supp. 1, The Program for the 50th Annual Meeting of the American Diabetes Association in Atlanta, Georgia, Abstract #66.

Scott, W. E., "Filler Research Studies Improve Papermaking Applications," *American Papermaker*, pp. 12–14, May 1987.

Shibata, Shozo et al., "Dual–Wavelength Spectrophotometry—Part 1. General Method," *Analytica Chimica Acta*, 46, pp. 271–279 (1969).

Shoucri, R. M., et al., "Some Observations on the Kinetics of the Jaffe Reaction for Creatinine," *Clinical Chemistry*, vol. 23, No. 9, pp. 1527–1530 (1977).

Soloniewicz, R. et al., "Spectrophotometric Determination of Reducing Sugars with Aromatic Nitro Compounds," Institute of General Chemistry, Technical University, Lodz, Poland, pp. 105–114 (1980).

Songer, T. J., "Health Insurance Characteristics in Families with IDDM Children," *Diabetes*, May 1990, vol. 39, Supp. 1, The Program for the 50th Annual Meeting of the American Diabetes Association in Atlanta, Georgia, Abstract #210.

Sonksen, P. H. et al., "Home Monitoring of Blood–Glucose—Method for Improving Diabetic Control," *The Lancet*, pp. 729–732, Apr. 8, 1978.

Spayd, R. W., et al., "Multilayer Film Elements for Clinical Analysis: Applications to Representative Chemical Determinations," *Clinical Chemistry*, vol. 24, No. 8, pp. 1343–1350 (1978).

Sundaram et al., "Routine Glucose Determination In Serum By Use Of An Immobilized Glucose Dehydrogenase Nylon–Tube Reactor," *Clinical Chemistry*, vol. 25, No. 8, (1979) pp. 1436–1439.

System Olli 3000, *Clinical Chemistry*, vol. 21, No. 6, p. 67 (1976).

Table, *Clinical Chemistry*, vol. 27, No. 1, p. 33 (1981).

Table 2. Visual Observation of the Spectral Output of Three Beckman TR's at the Exit Slit, *Clinical Chemistry*, vol. 21, No. 11, p. 1584 (1975).

Tideman, A. M., "Clinical Evaluation of a Hospital Blood Glucose Monitoring System," *Diabetes*, May 1990, vol. 39, Supp. 1, The Program for the 50th Annual Meeting of the American Diabetes Association in Atlanta, Georgia, Abstract #877.

Toren, E. C. Jr., et al., "Interface Instrumentation between Computer and Spectrophotometer for Reaction Rate Measurements," *Clinical Chemistry*, vol. 16, No. 3, pp. 215–221 (1970).

Walford, S. et al., "Self–Monitoring of Blood–Glucose—Improvement of Diabetic Control," *The Lancet*, pp. 732–735, Apr. 8, 1978.

Walker, E. A., et al., "What is the Present Practice of Quality Assurance for Bedside BGM in Health Care Facilities?," *Diabetes*, May 1990, vol. 39, Supp. 1, The Program for the 50th Annual Meeting of the American Diabetes Association in Atlanta, Georgia, Abstract #872.

Wilkman, M. J., "Evaluation of Nurse Accuracy of Bedside Glucose Monitoring with Two Systems," *Diabetes*, May 1990, vol. 39, Supp. 1, The Program for the 50th Annual Meeting of the American Diabetes Association in Atlanta, Georgia, Abstract #682.

Wylie–Rosett, J., et al., "Brief Diabetes Quality Assurance (QA) Checklist," *Diabetes*, May 1990, vol. 39, Supp. 1, The Program for the 50th Annual Meeting of the American Diabetes Association in Atlanta, Georgia, Abstract #866.

Zamzow, K., et al., "New Wearable Continuous Blood Glucose Monitor (BGM) and Artificial Pancreas (A)," *Diabetes*, May 1990, vol. 39, Supp. 1, The Program for the 50th Annual Meeting of the American Diabetes Association in Atlanta, Georgia, Abstract #20.

Zimmet, P. et al., "Computerized Assessment of Self–Monitored Blood Glucose Results Using a Glucometer Reflectance Photometer with Memory and Microcomputer," *Diabetes Research and Clinical Practice*, pp. 55–63 (1985).

Zollinger, H., "The Mechanism of Oxidative Coupling," *Azo and Diazo Chemistry Aliphatic and Aromatic Compounds*, 1961, pp. 243–248.

Billmeyer, F. W. Jr., et al., *Principles of Color Technology*, Second Edition, John Wiley & Sons, Inc. 1981.

Application of Near Infra Red Spectrophotometry to the Nondestructive Analysis of Foods: A Review of Experimental Results," *CRC Critical Reviews In Food Science And Nutrition*, Science and Nutrition, 18(3):203–30 (1983).

Villeneuve, M. E. et al., "Evaluating Blood Glucose Monitors," *American Journal of Nursing*, Nov. 1985, pp. 1258–1259.

Walter, B., "Dry Reagent Chemistries in Clinical Analysis," *Analytical Chemistry*, vol. 55, No. 4, Apr. 1983, pp. 498A–514A.

Sternberg, J. C. et al., "Spectrophotometric Analysis of Multicomponent Systems Using the Least Squares Method in Matrix Form: The Ergosterol Irradiation System," *Analytical Chemistry*, vol. 32, No. 1, Jan. 1960, pp. 84–90.

Chance, B., "Rapid and Sensitive Spectrophotometry. III. A Double Beam Apparatus," *Rev. Sci. Instru.*, 22, pp. 634–638 (1951).

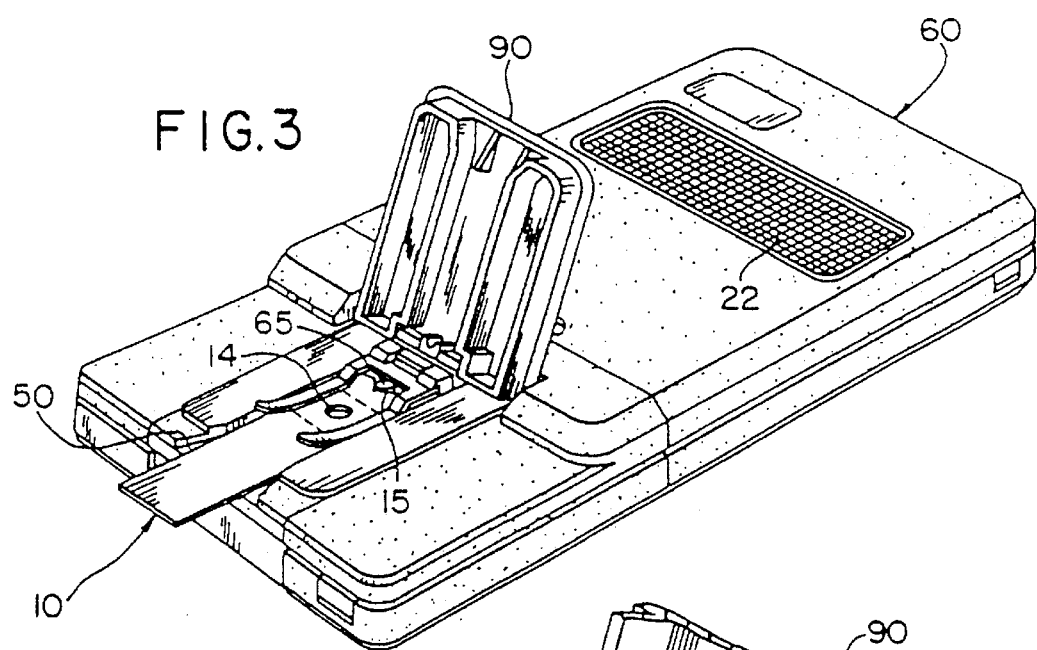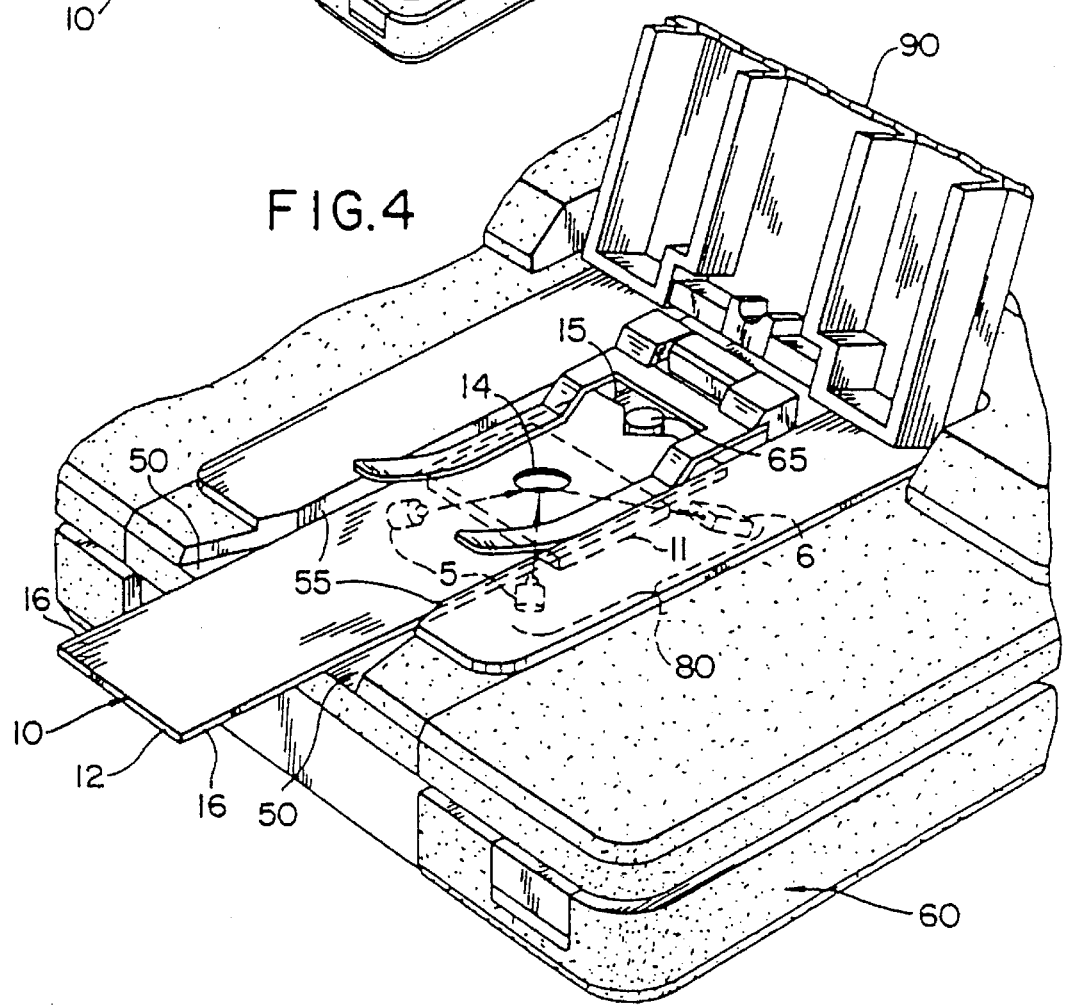

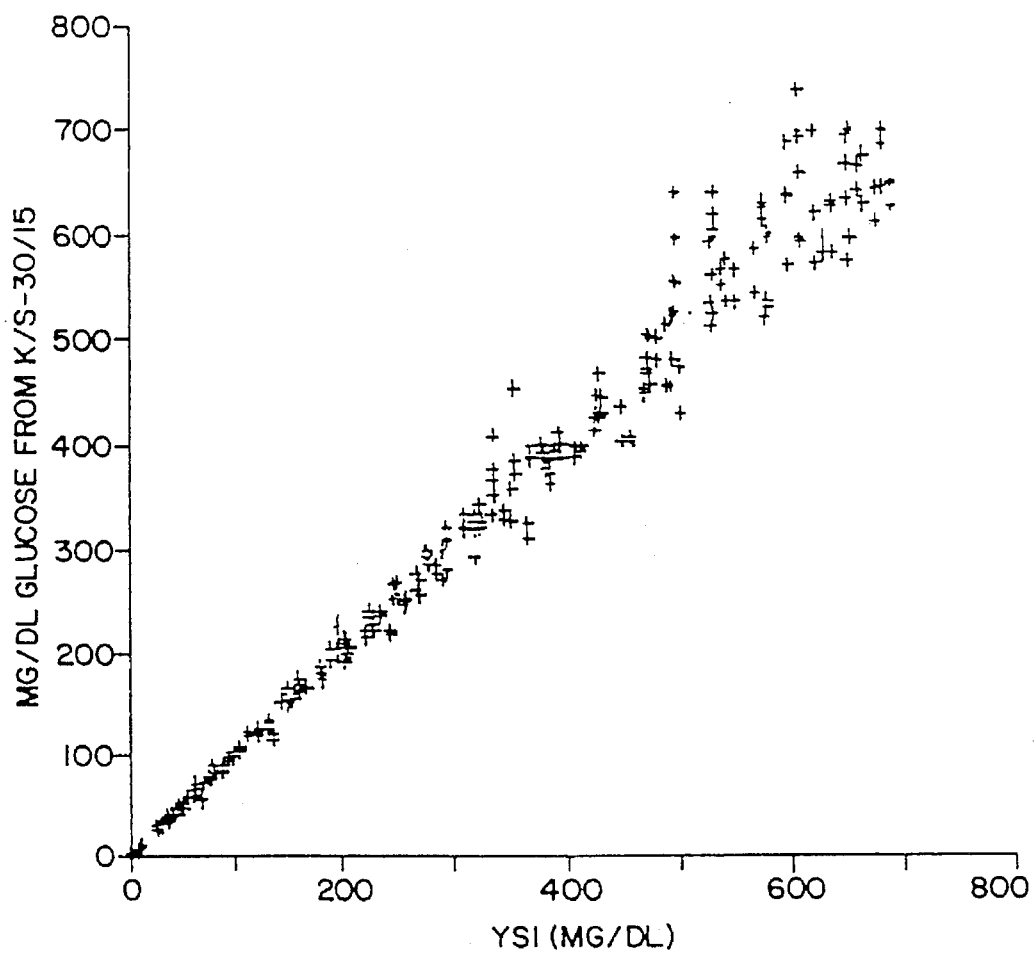

WHOLE BLOOD GLUCOSE TEST STRIP

This is a continuation of application Ser. No. 08/148,055, filed Nov. 5, 1993, now U.S. Pat. No. 5,426,032 which is a division of application Serial No. 08/006,859, filed on Jan. 21, 1993, now abandoned, which is a division of application Ser. No. 07/819,431, filed on Jan. 10, 1992, now abandoned, which is a division of application Ser. No. 07/187,602, filed on Apr. 28, 1988, now U.S. Pat. No. 5,179,005, which is a continuation-in-part of application Ser. No. 06/896,418, filed on Aug. 13, 1986, now U.S. Pat. No. 4,935,346.

This application is also directly related to U.S. Pat. No. 5,304,468, which issued on Apr. 19, 1994, from application Ser. No. 9,179, filed Jan. 26, 1993, which is a continuation of application Ser. No. 819,431, filed Jan. 10, 1992, and now abandoned, which is a division of application Ser. No. 187,602, filed Apr. 28, 1988, now U.S. Patent No. 5,179,005, which is a continuation in part of application Ser. No. 896,418, filed Aug. 13, 1986, now issued U.S. Pat. No. 4,935,346.

This application is also related to U.S. Pat. No. 5,049,487, which issued on Sep. 17, 1991, from application Ser. No. 154,983, filed Feb. 11, 1988, which is a division of application Ser. No. 896,418, filed Aug. 13, 1986, and now issued U.S. Pat. No. 4,935,346.

This application is also related to U.S. Pat. No. 5,059,394, which issued on Oct. 22, 1991, from application Ser. No. 154,941, filed Feb. 11, 1988, which is a division of application Ser. No. 896,418, filed Aug. 13, 1986, and now issued U.S. Pat. No. 4,935,346.

This application is also related to U.S. patent application Ser. No. 283,722, filed on Jul. 29, 1994, and now abandoned.

This application is also related to U.S. patent application No. (not yet assigned), filed on May 31, 1995, which is a Rule 60 continuation of application Ser. No. 08/408,064, filed Mar. 21, 1995, which is a continuation of pending allowed application Ser. No. 08/148,055, filed Nov. 5, 1993,[2] which is a division of application Ser. No. 08/006,859, filed Jan. 21, 1993, now abandoned, which is a division of application Ser. No. 07/819,431, filed Jan. 10, 1992, now abandoned, which is a division of application Ser. No. 07/187,602, filed Apr. 28, 1988, now U.S. Pat. No. 5,179,005, which is a continuation-in-part of application Ser. No. 06/896,418, filed Aug. 13, 1986, now U.S. Pat. No. 4,935,346.

[2] Patent application Ser. No. 08/148,055 is scheduled to issue on Jun. 20, 1995, as U.S. Pat. No. 5,426,032.

FIELD OF THE INVENTION

The present invention relates to a test device and method for the colorimetric determination of chemical and biochemical components (analytes) in aqueous fluids, particularly whole blood. In one preferred embodiment it concerns a test device and method for colorimetrically measuring the concentration of glucose in whole blood.

BACKGROUND OF THE INVENTION

The quantification of chemical and biochemical components in colored aqueous fluids, in particular colored biological fluids such as whole blood and urine and biological fluid derivatives such as blood serum and blood plasma, is of ever-increasing importance. Important applications exist in medical diagnosis and treatment and in the quantification of exposure to therapeutic drugs, intoxicants, hazardous chemicals and the like. In some instances, the amounts of materials being determined are either so miniscule—in the range of a microgram or less per deciliter—or so difficult to precisely determine that the apparatus employed is complicated and useful only to skilled laboratory personnel. In this case the results are generally not available for some hours or days after sampling. In other instances, there is often an emphasis on the ability of lay operators to perform the test routinely, quickly and reproducibly outside a laboratory setting with rapid or immediate information display.

One common medical test is the measurement of blood glucose levels by diabetics. Current teaching counsels diabetic patients to measure their blood glucose level from two to seven times a day depending on the nature and severity of their individual cases. Based on the observed pattern in the measured glucose levels, the patient and physician together make adjustments in diet, exercise and insulin intake to better manage the disease. Clearly, this information should be available to the patient immediately.

Currently a method widely used in the United States employs a test article of the type described in U.S. Pat. No. 3,298,789 issued Jan. 17, 1967 to Mast. In this method a sample of fresh, whole blood (typically 20–40 μl) is placed on an ethylcellulose-coated reagent pad containing an enzyme system having glucose oxidase and peroxidase activity. The enzyme system reacts with glucose and releases hydrogen peroxide. The pad also contains an indicator which reacts with the hydrogen peroxide in the presence of peroxidase to give a color proportional in intensity to the sample's glucose level.

Another popular blood glucose test method employs similar chemistry but in place of the ethylcellulose-coated pad employs a water-resistant film through which the enzymes and indicator are dispersed. This type of system is disclosed in U.S. Pat. No. 3,630,957 issued Dec. 28, 1971 to Rey et al.

In both cases the sample is allowed to remain in contact with the reagent pad for a specified time (typically one minute). Then in the first case the blood sample is washed off with a stream of water while in the second case it is wiped off the film. The reagent pad or film is then blotted dry and evaluated. The evaluation is made either by comparing color generated with a color chart or by placing the pad or film in a diffuse reflectance instrument to read a color intensity value.

While the above methods have been used in glucose monitoring for years, they do have certain limitations. The sample size required is rather large for a finger stick test and is difficult to achieve for some people whose capillary blood does not express readily.

In addition, these methods share a limitation with other simple lay-operator colorimetric determinations in that their result is based on an absolute color reading which is in turn related to the absolute extent of reaction between the sample and the test reagents. The fact that the sample must be washed or wiped off the reagent pad after the timed reaction interval requires that the user be ready at the end of the timed interval and wipe or apply a wash stream at the required time. The fact that the reaction is stopped by removing the sample leads to some uncertainty in the result, especially in the hands of the home user. Overwashing can give low results and underwashing can give high results.

Another problem that often exists in simple lay-operator colorimetric determinations is the necessity for initiating a timing sequence when blood is applied to a reagent pad. A user will typically have conducted a finger stick to obtain a blood sample and will then be required to simultaneously apply the blood from the finger to a reagent pad while initiating a timing circuit with his or her other hand, thereby requiring the use of both hands simultaneously. This is particularly difficult since it is often necessary to insure that the timing circuit is started only when blood is applied to the reagent pad. All of the prior art methods require additional manipulations or additional circuitry to achieve this result. Accordingly, simplification of this aspect of reflectance reading instruments is desirable.

The presence of red blood cells or other colored components often interferes with the measurements of these absolute values, thereby calling for exclusion of red blood cells in these two prior methods as they are most widely practiced. In the device of U.S. Pat. No. 3,298,789 an ethyl cellulose membrane prevents red blood cells from entering the reagent pad. Similarly, the water-resistant film of U.S. Pat. No. 3,630,957 prevents red blood cells from entering the pad. In both cases the rinse or wipe also acts to remove these potentially interfering red blood cells prior to measurement.

Accordingly, there remains a need for a system of detecting analytes in colored liquids, such as blood, that does not require removal of excess liquid from a reflectance strip from which a reflectance reading is being obtained.

SUMMARY OF THE INVENTION

Novel methods, compositions and apparatus are provided for diagnostic assays comprising a hydrophilic porous matrix containing a signal producing System and a reflectance measuring apparatus which is activated upon a change in reflectance of the matrix when fluid penetrates the matrix. The method comprises adding the sample, typically whole blood, to the matrix which filters out large particles, such as red blood cells, typically with the matrix present in the apparatus. The signal-producing system produces a product which further changes the reflectance of the matrix, which change can be related to the presence of an analyte in a sample.

Exemplary of the diagnostic assay system is the determination of glucose in the whole blood, where the determination is made without interference from the blood and without a complicated protocol subject to use error.

BRIEF DESCRIPTION OF THE DRAWINGS

The present invention can be more readily understood by reference to the following detailed description when read in conjunction with the attached drawings, wherein:

FIG. 3 is a perspective view of a preferred embodiment of the test device of the present invention emplaced within a measuring system;

FIG. 4 is an enlarged plan view of a preferred embodiment of the test device of the present invention emplaced within a measuring system;

FIGS. 7a, 7b, 7c and 7d are scattergrams of glucose values as measured by a second preferred embodiment of the present invention (called the double wavelength MPX system) plotted against Yellow Springs Instruments (YSI) glucose values.

DETAILED DESCRIPTION OF THE INVENTION

The Reagent Element

Figure 1:
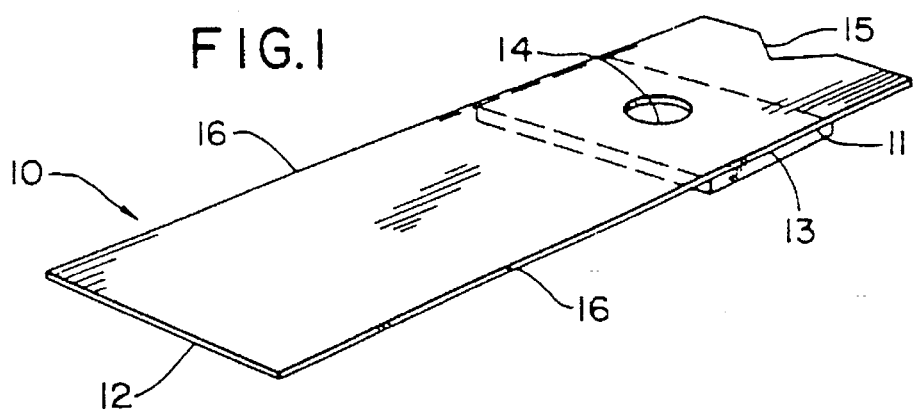
FIG. 1 is a perspective view of one embodiment of a test device containing the reaction pad to which the fluid being analyzed is applied.

The subject invention provides an improved rapid and simple methodology employing reliable and easy to operate apparatus for the determination of analytes such as glucose, particularly involving an enzyme substrate which results in the production of hydrogen peroxide as an enzyme product. The method involves applying to a porous matrix a small volume of whole blood, sufficient to saturate the matrix. It is to be noted that the present system is capable of determining glucose levels from optical readings of whole blood samples. Separation of plasma from blood in the sample is unnecessary, and the present invention avoids the requirement of this step. In addition, this system is capable of performing accurate readings as long as only a small volume saturates the matrix of the test strip. Above this threshold, the reading is volume independent.

Bound to the matrix are one or more reagents of a signal producing system, which results in the production of a product resulting in an initial change in the amount of reflectance of the matrix. The matrix is typically present in a reflectance-measuring apparatus when blood is applied. The liquid sample penetrates the matrix, resulting in an initial change in reflectance at the measurement surface. A reading is then taken at one or more times after the initial change in reflectance to relate the further change in reflectance at the measurement surface or in the matrix as a result of formation of the reaction product to the amount of analyte in the sample.

For measurements in blood, particularly glucose measurements, whole blood is typically used as the assay medium. The matrix contains an oxidase enzyme which produces hydrogen peroxide. Also contained in the matrix will be a second enzyme, particularly a peroxidase, and a dye system which produces a light-absorbing product in conjunction with the peroxidase. The light-absorbing product changes the reflectance signal of the matrix system. With whole blood, readings are taken at two different wavelengths, with the reading at one wavelength used to subtract out background interference caused by hematocrit, blood oxygenation, and other variables which may affect the result. Thus, the present invention is capable of analyzing samples of whole blood.

A reagent element is employed which comprises the matrix and the members of the signal producing system contained within the matrix. The reagent element may include other components for particular applications. The method requires applying a small volume of blood, which typically has not been subject to prior treatment (other than optional treatment with an anticoagulant), to the matrix. Timing of the measurement is activated or initialized by the apparatus' automatically detecting a change in reflectance of the matrix when fluid penetrates the matrix. The change in reflectance over a predetermined time period as a result of formation of reaction product is then related to the amount of analyte in a sample. The intensity of the light source used to analyze the sample is, of course, also carefully monitored and regulated, to insure the repeatability of the measurement.

The first component of the present invention to be considered is a reagent element, conveniently in the shape of a pad, comprising an inert porous matrix and the component or components of a signal-producing system, which system is capable of reacting with an analyte to produce a light-absorbing reaction product, impregnated into the pores of the porous matrix. The signal-producing system does not significantly impede the flow of liquid through the matrix.

In order to assist in reading reflectance, it is preferred that the matrix have at least one side which is substantially smooth and flat. Typically, the matrix will be formed into a thin sheet with at least one smooth, flat side. In use, the liquid sample being analyzed is applied to one side of the sheet whereby any assay compound present passes through the reagent element by means of capillary, wicking, gravity flow and/or diffusion actions. The components of the signal producing system present in the matrix will react to give a light absorbing reaction product. Incident light impinges upon the reagent element at a location other than the location to which the sample is applied. Light is thus reflected from the surface of the element as diffuse reflected light. This diffuse light is collected and measured, for example by the detector of a reflectance spectrophotometer. The amount of reflected light will be related to the amount of analyte in the sample, usually being an inverse function of the amount of analyte in the sample.

The Matrix

Each of the components necessary for producing the reagent element will be described in turn. The first component is the matrix itself.

The matrix will be a hydrophilic porous matrix to which reagents may be covalently or noncovalently bound. The matrix will allow for the flow of an aqueous medium through the matrix. It will also allow for binding of protein compositions to the matrix without significantly adversely affecting the biological activity of the protein, e.g., enzymatic activity of an enzyme. To the extent that proteins are to be covalently bound, the matrix will have active sites for covalent bonding or may be activated by means known to the art. The composition of the matrix will be reflective and will be of sufficient thickness to permit the formation of a light-absorbing dye in the void volume or on the surface to substantially affect the reflectance from the matrix. The matrix may be of a uniform composition or a coating on a substrate providing the necessary structure and physical properties.

The matrix will usually not deform on wetting, thus retaining its original conformation and size. The matrix will have a defined absorbance, so that the volume which is absorbed can be calibrated within reasonable limits, variations usually being maintained below about 50% preferably not greater than 10%. The matrix will have sufficient wet strength to allow for routine manufacture. The matrix will permit non-covalently bound reagents to be relatively uniformly distributed on the surface of the matrix.

As exemplary of matrix surfaces are polyamides, particularly with samples involving whole blood. The polyamides are conveniently condensation polymers of monomers of from 4 to 8 carbon atoms, where the monomers are lactams or combinations of diamines and di-carboxylic acids. Other polymeric compositions having comparable properties may also find use. The polyamide compositions may be modified to introduce other functional groups which provide for charged structures, so that the surfaces of the matrix may be neutral, positive or negative, as well as neutral, basic or acidic. Preferred surfaces are positively charged. It has been determined that this positive charge enhances both stability and shelf-life.

When used with whole blood, the porous matrix preferably has pores with an average diameter in the range of from about 0.1 to 2.0 µm, more preferably from about 0.6 to 1.0 µm. When the porous matrix contains pores having an average diameter of about 0.8 µm, the sample of blood will not cause a chromatographic effect. That is, the blood sample will not seek out the edges of the circular matrix. Rather, the blood remains seated within all the pores of the matrix and provides for a uniform readability of the entire matrix. In addition, this pore size maximizes the non-blotting effect of the blood. That is, the pore size is both adequately filled, but not overfilled, so that the hematocrit level of blood will not cause the sample to require blotting prior to reading of the sample. Also, it has been found that pores of this size are optimal when shelf-life and stability are taken into consideration.

A preferred manner of preparing the porous material is to cast the hydrophilic polymer onto a core of non-woven fibers. The core fibers can be any fibrous material that produce the described integrity and strength, such as polyesters and polyamides. The reagent that will form the light-absorbing reaction product, which is discussed later in detail, is present within the pores of the matrix but does not block the matrix so that the liquid portion of the assay medium, e.g. blood, being analyzed can flow through the pores of the matrix, while particles, such as erythrocytes, are held at the surface.

The matrix is substantially reflective so that it gives a diffuse reflectance without the use of a reflective backing. Preferably at least 25%, more preferably at least 50%, of the incident-light applied to the matrix is reflected and emitted as diffuse reflectance. A matrix of less than about 0.5 mm thickness is usually employed, with from about 0.01 mm to about 0.3 mm being preferred. A thickness of from about 0.1 mm to about 0.2 mm is most preferred, particularly for a nylon matrix.

Typically, the matrix will be attached to a holder in order to give it physical form and rigidity, although this may not be necessary. FIG. 1 shows one embodiment of the invention in which there is a strip 10 having a thin hydrophilic matrix pad 11 positioned at one end of a plastic holder or handle 12 by means of an adhesive 13 which directly and firmly attaches the reagent pad 11 to the handle 12. A hole 14 is present in the plastic holder 12 in the area to which reagent pad 11 is attached so that sample can be applied to one side of the reagent pad and light reflected from the other side.

A liquid sample to be tested is applied to pad 11. Generally, with blood being exemplary of a sample being tested, the reagent pad will be on the order of about 10 mm$^2$ to 100 mm$^2$ in surface area, especially 10 mm$^2$ to 50 mm$^2$ in area (or having a diameter of about 2 mm to about 10 mm), which is normally a volume that 5–10 microliters of sample will more than saturate. Of course, once saturation is reached at above the threshold of about 5–10 microliters, no other requirement of blood amount is necessary.

Diffuse reflectance measurements in the prior art have typically been taken using a reflective backing attached to or placed behind the matrix. No such backing is needed or will normally be present during the practice of the present invention, either as part of the reagent element or the reflectance apparatus.

As can be seen from FIG. 1, the support holds reagent pad 11 so that a sample can be applied to one side of the reagent pad 11 while light reflectance is measured from the side of the reagent pad 11 opposite the location where sample is applied.

Figure 2:
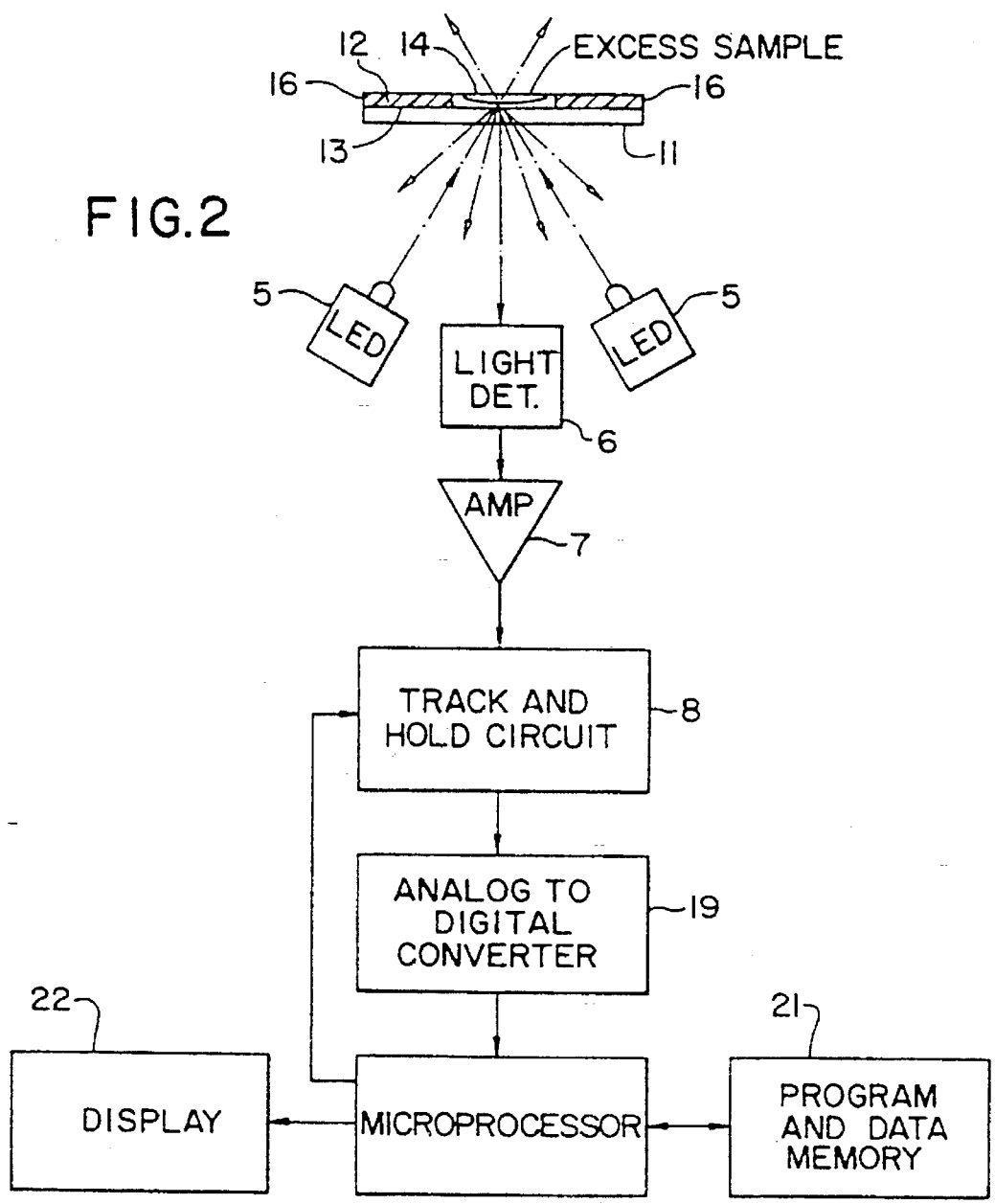
FIG. 2 is a block diagram schematic of an apparatus that can be employed in the practice of the invention.

FIG. 2 shows a system in which the reagent is applied to the side with the hole 14 in the backing handle 12 while light is reflected and measured on the other side of the reagent pad 11. Other structures than the one depicted may be employed. The pad 11 may take various shapes and forms, subject to the limitations provided herein. The pad 11 will be accessible on at least one surface and usually two surfaces.

The hydrophilic layer (reagent element) may be attached to the support by any convenient means, e.g., a holder, clamp or adhesives; however, in the preferred method it is bonded to the backing. The bonding can be done with any non-reactive adhesive, by a thermal method in which the backing surface is melted enough to entrap some of the material used for the hydrophilic layer, or by microwave or ultrasonic bonding methods which likewise fuse the hydrophilic sample pads to the backing. It is important that the bonding be such as to not itself interfere substantially with the diffuse reflectance measurements or the reaction being measured, although this is unlikely to occur as no adhesive need be present at the location where the reading is taken. For example, an adhesive 13 can be applied to the backing strip 12 followed first by punching hole 14 into the combined strip and adhesive and then applying reagent pad 11 to the adhesive in the vicinity of hole 14 so that the peripheral portion of the reagent pad attaches to the backing strip.

The Chemical Reagents

Any signal producing system may be employed that is capable of reacting with the analyte in the sample to produce (either directly or indirectly) a compound that is characteristically absorptive at a wavelength other than a wavelength at which the assay medium substantially absorbs.

Polyamide matrices are particularly useful for carrying out reactions in which a substrate-(analyte) reacts with an oxygen-utilizing oxidase enzyme in such a manner that a product is produced that further reacts with a dye intermediate to either directly or indirectly form a dye which absorbs in a predetermined wavelength range. For example, an oxidase enzyme can oxidize a substrate and produce hydrogen peroxide as a reaction product. The hydrogen peroxide can then react with a dye intermediate or precursor, in a catalysed or uncatalyzed reaction, to produce an oxidized form of the intermediate or precursor. This oxidized material may produce the colored product or react with a second precursor to form the final dye.

Nonlimiting examples of analyses and typical reagents include the following materials shown in the following list:

| Analyte and Sample Type | Reagents |
| --- | --- |
| Glucose in blood, serum, urine or other biological fluids, wine, fruit juices or other colored aqueous fluids. Whole blood is a particularly preferred sample type, as separation is time-consuming and impractical with home use. | Glucose Oxidase, Peroxidase and an Oxygen Acceptor<br><br>Oxygen Acceptors include:<br>O-dianisidine (1)<br>O-toluidine<br>O-tolidine (1)<br>Benzidine (1)<br>2,2'-Azinodi-(3-ethylbenzthiazoline sulphonic acid-(6)) (1)<br>3-Methyl-2-benzothiazolinone hydrazone plus N,N-dimethylaniline (1)<br>Phenyl plus 4-aminophenazone (1) |
| | Sulfonated 2,4-dichlorophenol plus 4-aminophenazone (2)<br>3-Methyl-2-benzothiazolinone hydrazone plus 3-(dimethylamino)benzoic acid (3)<br>2-Methoxy-4-allyl phenol (4)<br>4-Aminoantipyrene-dimethylaniline (5) |

(1) As reported Clinical chemistry, Richterich and Columbo, p. 367 and references cited therein.
(2) Analyst, 97, (1972) 142–5.
(3) Anal, Biochem., In, (1980) 389–397.
(4) Anal, Biochem., 79, (1977) 597–601.
(5) Clinica Chemica Acta, 75, (1977) 387–391
All incorporated herein by reference.

The Analysis Method

The analysis method of this invention relies on a change in absorbance, as measured by diffuse reflectance, which is dependent upon the amount of analyte present in a sample being tested. This change may be determined by measuring the change in the absorbance of the test sample between two or more points in time.

The first step of the assay to be considered will be application of the sample to the matrix. In practice, an analysis could be carried out as follows: First a sample of aqueous fluid containing an analyte is obtained. Blood may be obtained by a finger stick, for example. An excess over threshold matrix saturation in the area where reflectance will be measured (i.e., about 5–10 microliters) of this fluid is applied to the reagent element or elements of the test device. Simultaneous starting of a timer is not required (as is commonly required in the prior art), as will become clear below, due to the initialization procedure practiced by the present invention. Excess fluid can be removed, such as by light blotting, but such removal is also not required. The test device is typically mounted in an instrument for reading light absorbance, e.g., color intensity by reflectance, prior to application of the sample. Absorbance is measured at certain points in time after application of the sample. Absorbance refers in this application not only to light within the visual wavelength range but also outside the visual wavelength range, such as infrared and ultraviolet radiation. From these measurements of absorbance a rate of color development can be calibrated in terms of analyte level.

The Measuring Instrument

A suitable instrument, such as a diffuse reflectance spectrophotometer with appropriate software, can be made to automatically read reflectance at certain points in time, calculate rate of reflectance change, and, using calibration factors, output the level of analyte in the aqueous fluid. Such a device is schematically shown in FIG. 2 wherein a test device of the invention comprising backing 12 to which reagent pad 11 is affixed is shown. Light source 5, for example a high intensity light emitting diode (LED) projects a beam of light onto the reagent pad. A substantial portion (at least 25%, preferably at least 35%, and more preferably at least 50%, in the absence of reaction product) of this light is diffusively reflected from the reagent pad and is detected by light detector 6, for example a phototransistor that produces an output current proportional to the light it receives.

Light source 5 and/or detector 6 can be adapted to generate or respond to a particular wavelength light, if desired. The output of detector 6 is passed to amplifier 7, for example, a linear integrated circuit which converts the phototransistor current to a voltage. The output of amplifier 7 can be fed to track and hold circuit 8. This is a combination linear/digital integrated circuit which tracks or follows the analog voltage from amplifier 7 and, upon command from microprocessor 20, locks or holds the voltage at its level at that time.

Analog-to-digital converter 19 takes the analog voltage from track and hold circuit 8 and converts it to, for example, a twelve-bit binary digital number upon command of microprocessor 20. Microprocessor 20 can be a digital integrated circuit. It serves the following control functions: 1) timing for the entire system; 2) reading of the output of analog/digital converter 19; 3) together with program and data memory 21, storing data corresponding to the reflectance measured at specified time intervals; 4) calculating analyte levels from the stored reflectances; and 5) outputting analyte concentration data to display 22. Memory 21 can be a digital integrated circuit which stores data and the microprocessor operating program. Reporting device 22 can take various hard copy and soft copy forms. Usually it is a visual display, such as a liquid crystal (LCD) or LED display, but it can also be a tape printer, audible signal, or the like. The instrument also can include a start-stop switch and can provide an audible or visible time output to indicate times for applying samples, taking readings etc., if desired.

Reflectance Switching

In the present invention, the reflectance circuit itself can be used to initiate timing by measuring a drop in reflectance that occurs when the aqueous portion of the suspension solution applied to the reagent pad (e.g., blood) migrates to the surface at which reflectance is being measured. Typically, the measuring device is turned on in a "ready" mode in which reflectance readings are automatically made at closely spaced intervals (typically about 0.2 seconds) from the typically off-white, substantially dry, unreacted reagent strip. The initial measurement is typically made prior to penetration of the matrix by fluid being analyzed but can be made after the fluid has been applied to a location on the reagent element other than where reflectance is being measured. The reflectance value is evaluated by the microprocessor, typically by storing successive values in memory and then comparing each value with the initial unreacted value. When the aqueous solution penetrates the reagent matrix, the drop in reflectance signals the start of the measuring time interval. Drops in reflectance of 5–50% can be used to initiate timing, typically a drop of about 10%. In this simple way there is exact synchronization of assay medium reaching the surface from which measurements are taken and initiation of the sequence of readings, with no requirement of activity by the user.

Although the total systems described in this application are particularly directed to the use of polyamide matrices and particularly to the use of such matrices in determining the concentration of various sugars, such as glucose, and other materials of biological origin, there is no need to limit the reflectance switching aspect of the invention to such matrices. For example, the matrix used with reflectance switching may be formed from any water-insoluble hydrophilic material and any other type of reflectance assay.

Particular Application to Glucose Assay

A particular example with regard to detecting glucose in the presence of red blood cells will now be given in order that greater detail and particular advantage can be pointed out. Although this represents a preferred embodiment of the present invention, the invention is not limited to the detection of glucose in blood.

The use of polyamide surfaces to form the reagent element provides a number of desirable characteristics in the present invention. These are that the reagent element is hydrophilic (i.e., takes up reagent and sample readily), does not deform on wetting (so as to provide a flat surface for reflectance reading), is compatible with enzymes (in order to impart good shelf stability), takes up a limited sample volume per unit volume of membrane (necessary in order to demonstrate an extended dynamic range of measurements), and shows sufficient wet strength to allow for routine manufacture.

In a typical configuration, the method is carrier out using an apparatus consisting of a plastic holder and the reagent element (the matrix having the signal producing system impregnated therein.) The preferred matrix for use in preparing the reagent element is a nylon microfiltration membrane, particularly membranes made from nylon-66 cast on a core of non-woven polyester fibers. Numerous nylon microfiltration membranes of this class are produced commercially by the Pall Ultrafine Filtration Corporation, having average pore sizes from 0.1 to 3.0 microns. These materials shown mechanical strength and flexibility, dimensional stability upon exposure to water, and rapid wetting.

Many variations in specific chemical structure of the nylon are possible. These include unfunctionalized nylon-66 with charged end groups (sold under the trademark ULTRAPORE by Pall Ultrafine Filtration Corporation, "Pall"). Positive charges predominate below pH 6 while negative charges predominate above pH 6. In other membranes the nylon is functionalized before the membrane is formed to give membranes with different properties. Nylons functionalized with carboxy groups are negatively charged over a wide pH range (sold as CARBOXYDYNE by Pall). Nylons can also be functionalized with a high density of positively charged groups on its surface, typically quaternary amine groups, so that they display little variation in charge over a wide pH range (sold as POSIDYNE by Pall). Such materials are particularly well suited for the practice of the present invention.

It has been found that keeping the pH of the solution below 4.8 will help stabilize the enzymes in solution. The most efficient level of stability has been found at pH 4.0. This results in shelf life at room temperature of 12–18 months. Consequently, a strip with positively charged ions is most desirable.

It is also possible to use membranes having reactive functional groups designed for covalent immobilization of proteins (sold as BIODYNE IMMUNO AFFINITY membranes by Pall). Such materials can be used to covalently attach proteins, e.g. enzymes, used as reagents. Although all of these materials are usable, nylon having a high density of positively charged groups on its surface provide the best stability of reagents when formulated into a dry reagent pad. Unfunctionalized nylon gives the next best stability with the carboxylated nylons next best.

Desirable results can be obtained with pore sizes ranging from about 0.2–2.0 μm, preferably about 0.5–1.2 μm, and most preferably about 0.8 μm, when used with whole blood.

The form of the handle on which the reagent element is assembled is relatively unimportant as long as the handle allows access to one side of the reagent element by sample and to the other side of the reagent element by incident light whose reflectance is being measured. The handle also aids in inserting the reagent element into the absorbance measuring device so that it registers with the optical system. One example of a suitable handle is a mylar or other plastic strip to which a transfer adhesive such as 3M 465 or Y9460 transfer adhesive has been applied. A hole is punched into the plastic through the transfer adhesive. A reagent element, typically in the form of a thin pad, either containing reagents or to which reagents will later be added, is then applied to the handle by means of the transfer adhesive so that it is firmly attached to the handle in the area surrounding the hole that has been punched through the handle and the transfer adhesive.

Such a device is illustrated in FIG. 1, which shows a strip 10 having a reagent pad 11 attached to a Mylar handle 12 by means of adhesive 13. Hole 14 allows access of the sample or incident light to one side of reagent pad 11 while access to the other side of the reagent pad is unrestricted. All dimensions of the reagent pad and handle can be selected so that the reagent pad fits securely into a reflectance-reading instrument in proximal location to a light source and a reflected-light detector. Generally, dimensions of the hole are in the range of about 2–10 mm diameter, and that of the width of the handle about 15 mm. A 5 mm diameter hole 14 in the reagent strip shown in FIG. 1 works quite satisfactorily. Naturally, there is no particular limit on the minimum diameter of such a hole, although diameters of at least 2 mm are preferred for ease of manufacture, sample application, and light reflectance reading.

As further seen in FIGS. 3 and 4, the strip 10 can be optimally guided into a slot 50 on scanning machine 60. This is accomplished by placing a notch 15 in the strip 10 at about the midpoint of the top of strip 10. In so doing, the strip 10, when guided through sides 55 of slot 50, will arrive repeatably at the same location, to assure high assurance in test results. Such repeatability is accomplished by moving the notch 15 against post 65. The strip 10 will pivot around the post 65 at the notch 15, so that the edges 16 of the strip will fit within the sides 55 of the slot 50. This, of course, also repeatably aligns the hole 14 over the test center 80 comprising multiple LEDs 5 in the scanning machine 60. This insures that the hole 14 containing a blood sample will have uniform dosage of incident light for analysis.

Although a number of dyes could be used as indicators, the choice will depend upon the nature of the sample. It is necessary to select a dye having an absorbance at a wavelength different from the wavelength at which red blood cells absorb light, with Whole blood as the assay medium, or other contaminants in the solution being analyzed with other assay media. The MBTH-DMAB dye couple (3-methyl-2-benzothiazolinone hydrazone hydrochloride and 3-dimethylaminobenzoic acid), although being previously described as suitable for color development for peroxidase labels in enzyme immunoassays, has never been used in a commercial glucose measuring reagent. This dye couple gives greater dynamic range and shows improved enzymatic stability as compared to traditional dyes used for glucose measurement, such as benzidine derivatives. This enzymatic stability also makes the-MBTH-DMAB dye couple especially desirable in order to insure longer shelf life of the test strips. Furthermore, the MBTH-DMAB dye couple is not carcinogenic, a characteristic of most benzidine derivatives.

Another dye couple that can be used in the measurement of glucose is the AAP-CTA (4-aminoantipyrene and chromotropic acid) couple. Although this couple does not provide as broad a dynamic range as MBTH-DMAB, it is stable and suitable for use in the practice of the present invention when measuring glucose. Again, the AAP-CTA dye couple provides an expanded dynamic range and greater enzymatic activity stability than the more widely used benzidine dyes.

The use of the MBTH-DMAB couple allows for correction of hematocrit and degree of oxygenation of blood with a single correction factor. The more typically used benzidine dyes do not permit such a correction. The MBTH-DMAB dye forms a chromophore that absorbs at approximately 635 nm but not to any significant extent at 700 nm. Slight variations in measuring wavelengths (± about 10 nm) are permitted. At 700 nm both hematocrit and degree of oxygenation can be measured by measuring blood color. Furthermore, light emitting diodes (LED) are commercially available for both 635 nm and 700 nm measurements, thereby simplifying mass-production of a device. By using the preferred membrane pore size described above and the subject reagent formulation, both hematocrit and oxygenation behavior can be corrected by measuring at the single 700 nm wavelength.

Two additional conditions were found to provide particular stability and long shelf life for a glucose oxidase/peroxidase formulation on a polyamide matrix. Storage is enhanced at a pH in the range of 3.8 to 5.0 preferably about 3.8 to 4.3, most preferably about 4.0. Similarly, unexpectedly good storage and stability was found with mixture of a concentrated buffer system to the the reagents found in the matrix. The most effective buffer was found to be a 10% weight citrate buffer, with concentrations from about 5–15% being effective. These are weight/volume percentages of the solution in which the reagents are applied to the matrix. Other buffers can be used on the same molar basis. Greatest stability was achieved using a low pH, preferably about pH 4, an MBTH-DMAB dye system, and a high enzyme concentration of approximately 500–1000 M/ml of application solution. As previously indicated, such strips prepared using these parameters result in shelf life of about 12–18 months.

In preparing the MBTH-DMAB reagent and the enzyme system that forms the remainder of the signal producing system, it is not necessary to maintain exact volumes and ratios although the suggested values below give good results. Reagents are readily absorbed by the matrix pad when the glucose oxidase is present in a solution at about 27–54% by volume, the peroxidase is present at a concentration of about 2.7–5.4 mg/ml, MBTH is present at a concentration of about 4–8 mg/ml, and DMAB is present at a concentration of about 8–16 mg/ml. The DMAB-MBTH weight ratio is preferably maintained in the range of 1:1 to 4:1, preferably about 1.5:1 to 2.5:1, most preferably about 2:1.

The basic manufacturing techniques for the reagent element are, once established, straightforward. The membrane itself is strong and stable, particularly when a nylon membrane of the preferred embodiment is selected. Only two solutions are necessary for applying reagent, and these solutions are both readily formulated and stable. The first generally contains the dye components and the second generally contains the enzymes. When using the MBTH-DMAB dye couple, for example, the individual dyes are dissolved in an aqueous organic solvent, typically a 1:1 mixture of acetonitrile and water. The matrix is dipped into the solution, excess liquid is removed by blotting, and the matrix is then dried, typically at 50° C.–60° C. for 10–20 minutes. The matrix containing the dyes is then dipped into an aqueous solution containing the enzymes. A typical formulation would contain the peroxidase and glucose oxidase enzymes as well as any desired buffer, preservative, stabilizer, or the like. The matrix is then blotted to remove excess liquid and dried as before. A typical formulation for the glucose reagent is as follows:

Dye dip

Combine:

40 mg MBTH, 80 mg DMAB, 5 ml acetonitrile, and 5 ml water.

Stir until all solids are dissolved and pour onto a glass plate or other flat surface. Dip a piece of Posidyne membrane (Pall Co.), blot off excess liquid, and dry at 56° C. for 15 minutes.

Enzyme dip

Combine:

6 ml water, 10 mg EDTA, disodium salt, 200 mg of polypeptide sold by SIGMA® Chemical Company, St. Louis, Mo., under the trade name Sigma Poly Pep™, low viscosity, 0.668 g sodium citrate, 0.523 g citric acid, 2.0 ml 6 wt % of medium viscosity copolymer of polymethylvinyl ether/maleic anhydride, sold by the GAF Corporation, Wayne, N.J., under the trade name GAF Gantrez™ AN-139 dissolved in water 30 mg horseradish peroxidase, 100 units/mg, and 3.0 ml glucose oxidase, 2000 units/ml.

Stir until all solids are dissolved and pour onto a glass plate or other flat surface. Dip a piece of membrane previously impregnated with dyes, blot off excess liquid, and dry at 56° C. for 15 minutes.

The electronic apparatus used to make the reflectance readings minimally contains a light source, a reflected light detector, an amplifier, an analog to digital converter, a microprocessor with memory and program, and a display device, as seen in FIG. 2.

The light source typically consists of a light emitting diode (LED). Although it is possible to use a polychromatic light source and a light detector capable of measuring at two different wavelengths, a preferred apparatus would contain two LED sources or a single diode capable of emitting two distinct wavelengths of light. Commercially available LEDs producing the wavelengths of light described as being preferred in the present specification include a Hewlett Packard HLMP-1340 with an emission maximum at 635 nm and a Hewlett Packard QEMT-1045 with a narrow-band emission maximum at 700 nm. Suitable commercially available light detectors include a Hammamatsu 5874-18K and a Litronix BPX-65.

Although other methods of taking measurements are feasible, the following method has provided the desired results. Readings are taken by the photodetector at specified intervals after timing is initiated. The 635 nm LED is powered only during a brief measuring time span that begins approximately 20 seconds after the start time as indicated by the previously described reflectance switching system. If this reading indicates that a high level of glucose is present in the sample, a 30-second reading is taken and used in the final calculation in order to improve accuracy. Typically, high levels are considered to begin at about 250 mg/dl. The background is corrected with a 700 nm reading taken about 15 seconds after the start of the measurement period. The reading from the photodetector is integrated over the interval while the appropriate LED is activated, which is typically less than one second. The raw reflectance readings are then used for calculations performed by the microprocessor after the signal has been amplified and converted to a digital signal. Numerous microprocessors can be used to carry out the calculation. An AIM65 single-board microcomputer manufactured by Rockwell International has proven to be satisfactory.

Figure 5:
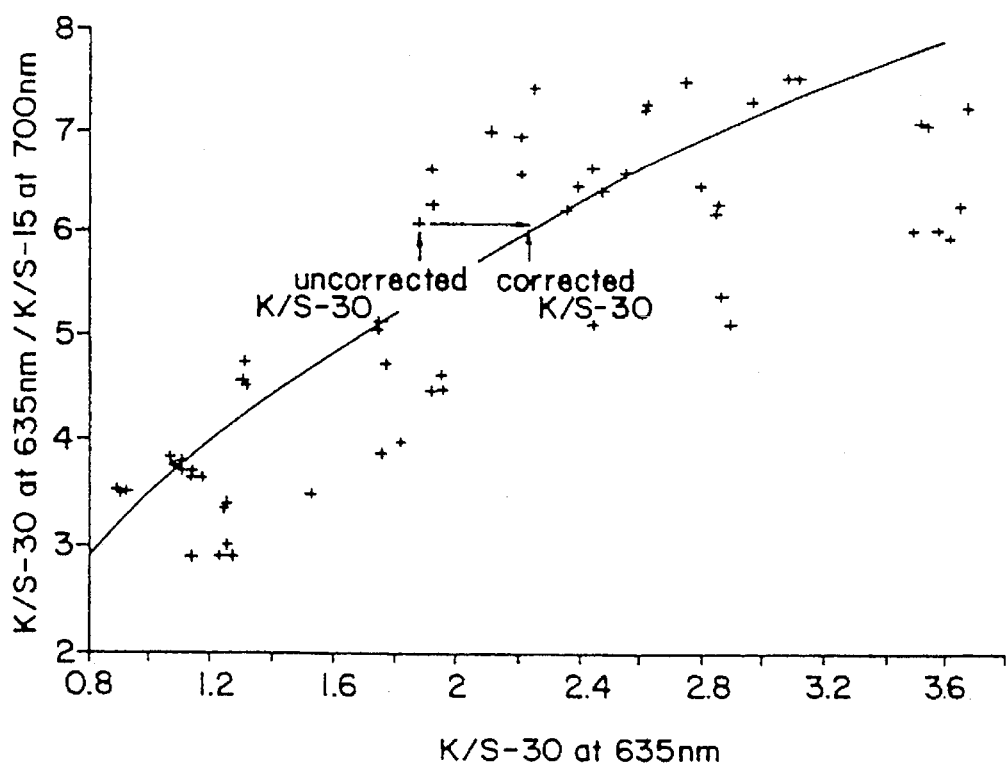
FIG. 5 is a graph plotting a second order correction to eliminate errors due to chromatography effects during the use of the present invention.

The present methods and apparatuses allow a very simple procedure with minimum operational steps on the part of the user. In use, the reagent strip 10 is placed in the detector so that the hole 14 in the strip 10 registers with the optics of the detecting system. The above-described notch 15/post 65 system, as seen in FIGS. 4 and 5 works nicely to accomplish such alignment. A removable cap or other cover 90 is placed over the optics and strip to shield the assembly from ambient light. This is done to enhance reading of the strip 10. While the initilization process can begin in light, direct sunlight or high intensity room light tends to inhibit results. The cap 90 insures that direct light does not hit the reagent strip 10. The cap 90 need not be light-tight, only enough to protect the strip 10 from direct light.

The measurement sequence is then initiated by pressing a button on the measuring apparatus that activates the microcomputer to take a measurement of reflected light from the unreacted reagent pad, called an $R_{dry}$ reading. The cap 90 is then removed and a drop of blood is applied to the reagent strip 10, typically while the reagent strip 10 is registered with the optics and the reading device. It is preferred that the reagent strip be left in register with the optics in order to minimize handling. The cap 90 is then closed.

The instrument is capable of sensing the application of blood or other sample by a decrease in the reflectance when the sample passes through the matrix and reflected light is measured on the opposite side. The decrease in reflectance initiates a timing sequence which is described in detail at other locations in this specification. The cap 90 should be replaced within 15 seconds of sample application, although this time may vary depending on the type of sample being measured.

Results are typically displayed at approximately 30 seconds after blood application when a blood glucose sample is being measured, although a 20 second reaction is permissible for glucose samples having a concentration of glucose of less than 250 mg/dl. If other samples are being measured, suitable times for displaying the result may differ and can be readily determined from the characteristics of the reagent/sample selected.

A particularly accurate evaluation of glucose level (or any other analyte being measured) can be made using the background current, i.e., the current from the photo detector with power on but with no light reflected from the reagent pad, in order to make a background correction. It has been demonstrated that over a 2–3 month period that this value does not change for a particular instrument prepared according to the preferred embodiments of this specification, and it is possible to program this background reading into the computer memory as a constant.

With a slight modification of the procedure, however, this value can be measured (or normalized) with each analysis for more accurate results. Each LED is turned on prior to placement of the blood sample on the reagent strip 10 but with the reagent strip 10 in place. A reflectance value of the strip 10 is then measured, with the reagent strip 10 in place and the light protective cap 90 closed. If this measurement is different than the original measurement of the reflectance value, power to the LED is increased so that the reflectance will be the same. This insures that the measurement of blood glucose content is being made on the same repeatable scale for each blood glucose reading.

The reason for instituting this method is twofold. First, the intensity of light emitting diodes will vary greatly from LED to LED, even when all the measuring LEDs are new. Second, the LED efficiency will vary with both temperature and the life of the LED. With this method, results are repeatable on the same scale.

The raw data necessary for calculating a result in a glucose assay are a background current reported as background reflectance, $R_b$, as described above; a reading of the unreacted test strip, $R_{dry}$, which is about 95% opaque to light and is also described above; and an end point measurement. Using the preferred embodiments described herein, the end point is not particularly stable and must be precisely timed from the initial application of blood. However, the meter as described herein performs this timing automatically. For glucose concentrations below 250 mg/dl, a suitably stable end point is reached in 20 seconds, and a final reflectance, $R_{20}$, is taken. For glucose concentrations up to 450 mg/dl, a 30-second reflectance reading, $R_{30}$, is adequate. Although the system described herein displays good differentiation up to 800 mg/dl of glucose, the measurement is somewhat noisy and inaccurate above 450 mg/dl, although not so great as to cause a significant problem. Longer reaction times should provide more suitable readings for the higher levels of glucose concentration.

The 700 nm reflectance reading for the dual wavelength measurement is typically taken at 15 seconds ($R_{15}$). By this time blood will have completely saturated the reagent pad. Beyond 15 seconds the dye reaction continues to take place and is sensed, to a small part, by a 700 nm reading. Accordingly, since dye absorption by the 700 nm signal is a disadvantage, readings beyond 15 seconds are ignored in the calculations.

The raw data described above are used to calculate parameters proportional to glucose concentration which can be more easily visualized than reflectance measurements. A logarithmic transformation of reflectance analogous to the relationship between absorbance and analyte concentration observed in transmission spectroscopy (Beer's Law) can be used if desired. A simplification of the Kubelka-Monk equations, derived specifically for reflectance spectroscopy, have proven particularly useful. In this derivation K/S is related to analyte concentration with K/S defined by Equation 1.

$$K/S-t=(1 \times R^*t)^2/(2 \times R^*t) \tag{1}$$

$R^*t$ is the reflectivity taken at a particular end point time, t, and is the absorbed fraction of the incident light beam described by Equation 2, where $R_t$ is the end point reflectance, $R_{20}$ or $R_{30}$.

$$R^*t=(R_t-R_b)/(R_{dry}-R_b) \tag{2}$$

$R^*t$ varies from 0 for no reflected light ($R_b$) to 1 for total reflected light ($R_{dry}$). The use of reflectivity in the calculations greatly simplifies meter design as a highly stable source and a detection circuit become unnecessary since these components are monitored with each $R_{dry}$ and $R_b$ measurement.

For a single wavelength reading K/S can be calculated at 20 seconds (K/S-20) or 30 seconds (K/S-30). The calibration curves relating these parameters to YSI (Yellow Springs Instruments) glucose measurements can be precisely described by the third order polynomial equation outlined in Equation 3.

$$YSI=a_0+a_1(K/S)+a_2(K/S)^2+a_3(K/S)^3 \tag{3}$$

The coefficients for these polynomials are listed in Table 1.

TABLE 1

Coefficients for Third Order Polynomial Pit of Single Wavelength Calibration Curves

|  | K/S-20 | K/S-30 |
| --- | --- | --- |
| $a_0$ | −55.75 | −55.25 |
| $a_1$ | 0.1632 | 0.1334 |
| $a_2$ | $-5.765 \times 10^{-5}$ | $-2.241 \times 10^{-5}$ |
| $a_3$ | $2.58 \times 10^{-8}$ | $1.20 \times 10^{-8}$ |

The single chemical species being measured in the preferred embodiments is the MBTH-DMAB inamine dye and the complex matrix being analyzed is whole blood distributed on a 0.8 µ Posidyne™ membrane. A review entitled "Application of Near Infra Red Spectrophotometry to the Nondestructive Analysis of Foods: A Review of Experimental Results", *CRC Critical Reviews in Food Science and Nutrition*, 18(3) 203–30 (1983), describes the use of instruments based on the measurement of an optical density difference $\Delta OD$ ($\lambda_a-\lambda_b$) where $OD\lambda_a$ is the optical density of the wavelength corresponding to the absorption maximum of a component to be determined and $OD\lambda_b$ is the optical density at a wavelength where the same component does not absorb significantly.

The algorithm for dual wavelength measurement is by necessity more complex than for single wavelength measurement but is much more powerful. The first order correction applied by the 700 nm reading is a simple subtraction of background color due to blood. In order to make this correction, a relationship between absorbance at 635 nm and 700 nm due to blood color can be and was determined by measuring blood samples with 0 mg/dl glucose over a wide range of blood color. The color range was constructed by varying hematocrit, and fairly linear relationships were observed. From these lines the K/S-15 at 700 nm was normalized to give equivalence to the K/S-30 at 635 nm. This relationship is reported in Equation 4, where K/S-15n is the normalized K/S-15 at 700 nm.

$$K/S\text{-}15n=(K/S\text{-}15 \times 1.54)-0.133 \tag{4}$$

Note that the equivalence of the normalized 700 nm signal and the 635 nm signal is only true at zero glucose. The expressions from which the calibration curves were derived are defined by Equations 5 and 6.

$$K/S\text{-}20/15=(K/S\text{-}20)-(K/S\text{-}15n) \tag{5}$$

$$K/S\text{-}30/15=(K/S\text{-}30)-(K/S\text{-}15n) \tag{6}$$

These curves are best fit by fourth-order polynomial equations similar to Equation 3 to which a fourth-order term in K/S is added. The computer-fit coefficients for these equations are listed in Table 2.

TABLE 2

Coefficients for Fourth-Order Polynomial Fit of Dual Wavelength Calibration Curves

|  | K/S-20/15 | K/S-30/15 |
| --- | --- | --- |
| $a_0$ | −0.1388 | 1.099 |
| $a_1$ | 0.1064 | 0.05235 |
| $a_2$ | $6.259 \times 10^{-5}$ | $1.229 \times 10^{-4}$ |
| $a_3$ | $-6.12 \times 10^{-8}$ | $-5.83 \times 10^{-8}$ |
| $a_4$ | $3.21 \times 10^{-11}$ | $1.30 \times 10^{-11}$ |

A second order correction to eliminate errors due to chromatography effects has also been developed. Low hematocrit samples have characteristically low 700 nm readings compared to higher hematocrit samples with the same 635 nm reading. When the ratio of (K/S-30)/(K/S-15) is plotted versus K/S-30 over a wide range of hematocrits and glucose concentrations, the resulting line on the graph indicates the border between samples which display chromatography effects (above the curve) and those that do not (below the curve). The K/S-30 for the samples above the curve are corrected by elevating the reading to correspond to a point on the curve with the same (K/S-30)/(K/S-15), as demonstrated by the correction made in FIG. 5.

The correction factors reported above were tailored to fit a single instrument and a limited number of reagent preparations. The algorithm can be optimized for an individual instrument and reagent in the same manner that is described above.

In summary, the system of the present invention minimizes operator actions and provides numerous advantages over prior art reflectance-reading methods. When compared to prior methods for determining glucose in blood, for example, there are several apparent advantages. First, the amount of sample required to saturate the thin reagent pad is small (typically 5–10 microliters), and is of course, volume independent once the threshold volume of blood is supplied to the reagent pad. Second, operator time required is only that necessary to apply the sample to the thin hydrophilic layer and close the cover (typically 4–7 seconds). Third, no simultaneous timing start is required. Fourth, whole blood can be used. The method does not require any separation or utilization of red-cell-free samples and likewise can be used with other deeply colored samples. Fifth, via the reflectance reading and normalization techniques applied in the present invention the system provides reliable, accurate, repeatable readings for the lifetime of the scanning system.

Several unobvious advantages arise as a result of the practice of the present invention with whole blood. Normally, aqueous solutions (like blood) will penetrate a hydrophilic membrane to give a liquid layer on the opposite side of the membrane, a surface that is then not suited for a reflectance measurement. It has been discovered, however, that blood, apparently because of interactions of red blood cells and proteins in the blood with the matrix, will wet the polyamide matrix without having an excess liquid penetrate the porous matrix to interfere with the reflectance reading on the opposite side of the matrix.

Furthermore, the thin membranes used in the present invention would be expected when wet to transmit light and return only a weak signal to the reflectance measuring device. Prior teachings have generally indicated that a reflective layer is necessary behind the matrix in order to reflect sufficient light. In other cases a white pad has been placed behind the reagent pad prior to color measurement. In the present case, neither a reflective layer nor a white pad is required. In fact, the invention is typically carried out with a light-absorbing surface behind the reagent element when incident light is impinged upon the matrix. This is accomplished using a light absorbing surface behind the reagent element, coupled with measuring reflectance at two different wavelengths. It allows acceptable reflectance measurements to be obtained without removal of excess liquid from the matrix, thereby eliminating a step typically required by previous teachings.

The invention now being generally described, the same will be better understood by reference to the following specific examples which are presented for purposes of illustration only and are not to be considered limiting of the invention unless so specified.

EXAMPLE I

Reproducibility

One male blood sample (having a hematocrit level of 45) was used to collect the reproducibility data using the presently preferred embodiment of the system, called the MPX system. The results are set forth in Tables 3–5.

TABLE 3

Reproducibility of a Single Wavelength System

| ***YSI | Average (mg/dl) | | *S.D. (mg/dl) | | % C.V.** | |
|---|---|---|---|---|---|---|
| (mg/dl) | 20 sec. | 30 sec | 20 sec | 30 sec | 20 sec. | 30 sec. |
| 25 | 23.1 | 23.0 | 2.1 | 2.04 | 9.1 | 9.0 |
| 55 | 53.3 | 53.2 | 3.19 | 3.32 | 6.0 | 6.3 |
| 101 | 101 | 101 | 3.0 | 3.3 | 3.0 | 3.0 |
| 326 | 326.6 | 327 | 13.3 | 9.8 | 4.1 | 3.0 |
| 501 | | 503 | | 17.1 | | 3.4 |
| 690 | | 675 | | 28 | | 4.15 |
| 810 | | 813 | | 37 | | 4.5 |

*S.D. = Standard Deviation
**% C.V. = Covariance (measured by percentage)
***YSI = Yellow Spring Instrument Glucose reading

TABLE 4

Reproducibility of a Dual Wavelength System

| ***YSI | Average (mg/dl) | | *S.D. (mg/dl) | | % C.V.** | |
|---|---|---|---|---|---|---|
| (mg/dl) | 20 sec. | 30 sec | 20 sec | 30 sec | 20 sec. | 30 sec. |
| 25 | 25 | 27 | 1.34 | 1.55 | 5.4 | 5.7 |
| 55 | 55 | 57.4 | 2.58 | 2.62 | 4.7 | 4.6 |
| 101 | 101 | 101.5 | 2.55 | 2.18 | 2.5 | 2.1 |
| 326 | 332 | 330 | 15.0 | 7.1 | 4.5 | 2.1 |
| 501 | | 505 | | 21.3 | | 4.2 |
| 690 | | 687 | | 22.8 | | 3.3 |
| 810 | | 817 | | 30.4 | | 3.7 |

TABLE 5

Reproducibility of a 3.0 mm Diameter Aperture

| | % C.V. | |
|---|---|---|
| YSI (mg/dl) | 4.7 mm | 3.0 mm |
| 55–100 | 4.8 | 4.9 |
| 300 | 3.0 | 5.0 |
| 600 | 3.8 | 5.5 |
| avg. | 3.9 | 5.1 |

The blood was divided into aliquots and spiked with glucose across a range of 25–800 mg/dl. Twenty determinations were made at each glucose test level from strips taken at random from a 500 strip sample (Lot FJ4-49B). The results of this study lead to the following conclusions:

1. Single vs. Dual Wavelength:

The average covariance for the 30-second dual result was 3.7% vs. 4.8% for the 30-second single wavelength result, an improvement of 23% across a glucose range of 25–810 mg/dl. There was a 33% improvement in covariance in the 25–326 mg/dl glucose range. Here the covariance decreased from 5.4% to 3.6%, a significant improvement in the most used range. The 20-second dual wavelength measurement gave similar improvements in covariance compared to the single wavelength measurement in the 25–326 mg/dl range (Tables 3 and 4).

2. Dual Wavelenth, 20 vs. 30-second Result:

The average covariance for a 20-second result in the 25–100 mg/dl range is nearly identical to the 30-second reading, 4.2% vs. 4.1%. However, at 326 mg/dl the 30-second reading has a covariance of 2.1% and the 20-second result a covariance of 4.5%. As was seen in the K/S-20 response curve, the slope begins to decrease sharply above 250 mg/dl. This lead to poor reproducibility at glucose levels greater than 300 for the 20-second result. From this reproducibility data the cutoff for the 20-second result is somewhere between 100 and 326 mg/dl. A cutoff of 250 mg/dl was later determined from the results of the recovery study set forth in Example II.

3. Aperture Size:

A smaller optics aperture size, 3.0 mm, was investigated. Initial experimentation using a 10 replicate, hand-dipped disk sample did show improved covariances with the 3.0 mm aperture, apparently because of easier registration with the system optics. However, when machine-made roll membrane was used, the average (Table 5) of the larger aperture, 4.7 mm, was 3.9% vs. an average covariance for the 3.0 mm aperture of 5.1%. This 30% increase was probably due to the uneven surface of the roll membrane lot as discussed below.

EXAMPLE II

Recovery:

For comparison of the present preferred method called MPX against a typical prior art method using a Yellow Springs Instrument Model 23A glucose analyzer manufactured by Yellow Springs Instrument Co., Yellow Springs, Ohio (YSI), blood from 36 donors was tested. The donors were divided equally between males and females and ranged in hematocrit from 35 to 55%. The blood samples were used within 30 hours of collection, with lithium heparin as the anti-coagulant. Each blood sample was divided into aliquots and spiked with glucose to give 152 samples in the range of 0–700 mg/dl glucose. Each sample was tested in duplicate for a total of 304 data points.

Figure 6A:
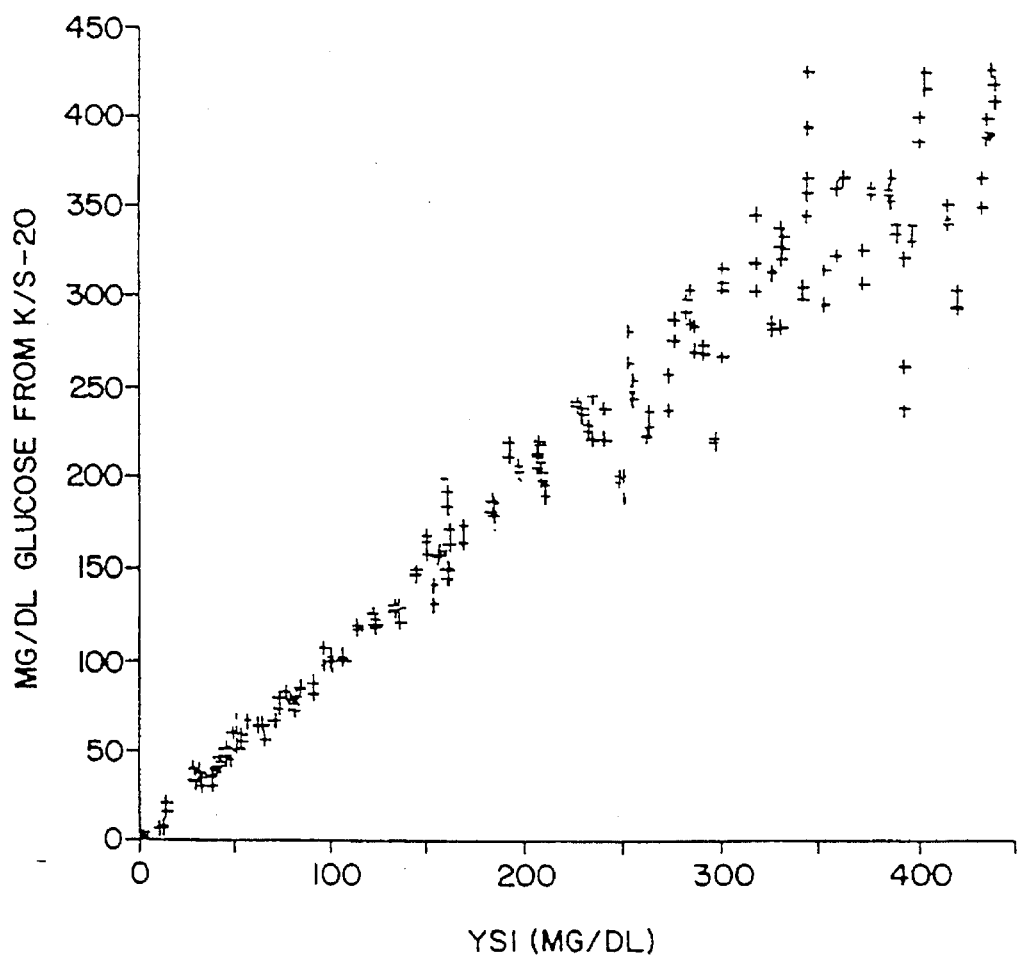
FIGS. 6a and 6b are scattergrams of glucose values as measured by a preferred embodiment of the present invention (called the single wavelength MPX system) plotted against Yellow Springs Instruments (YSI) glucose values.
Figure 6B:
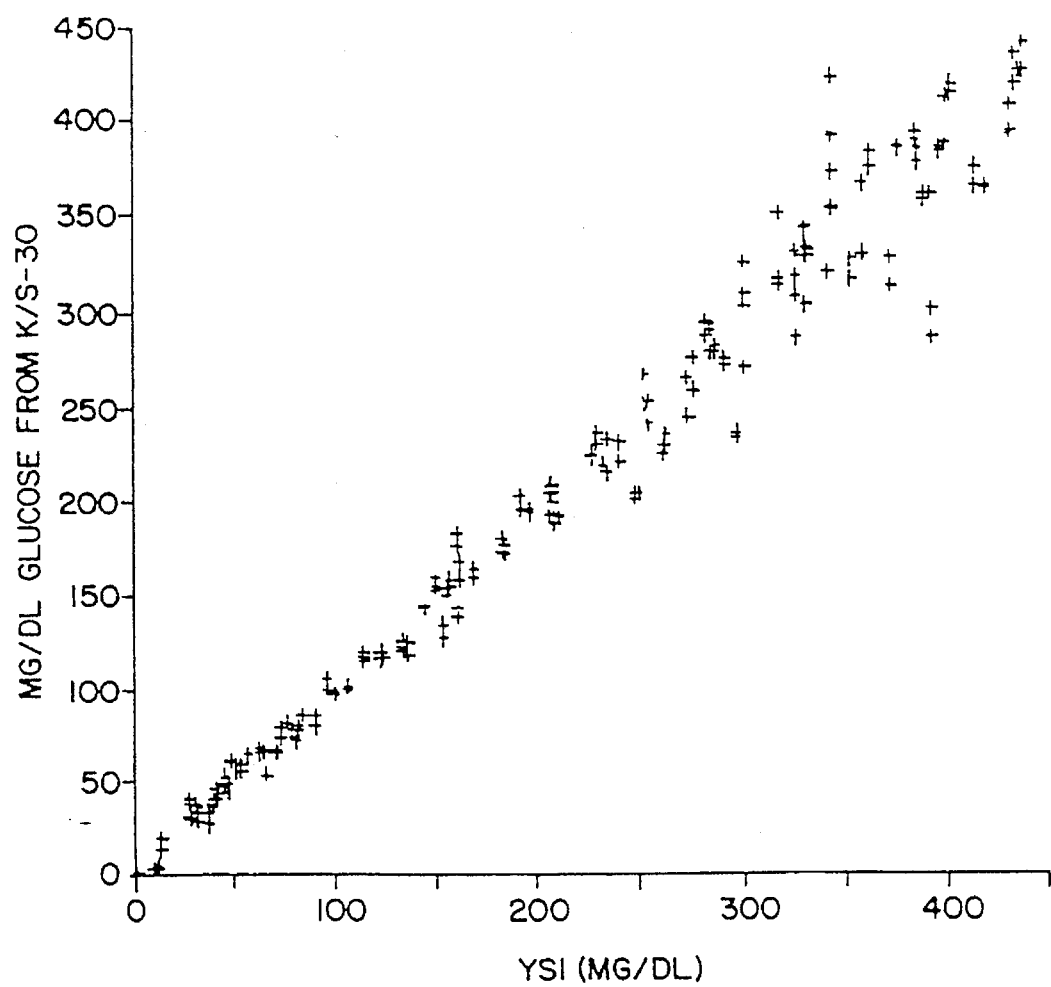
Figure 7A:
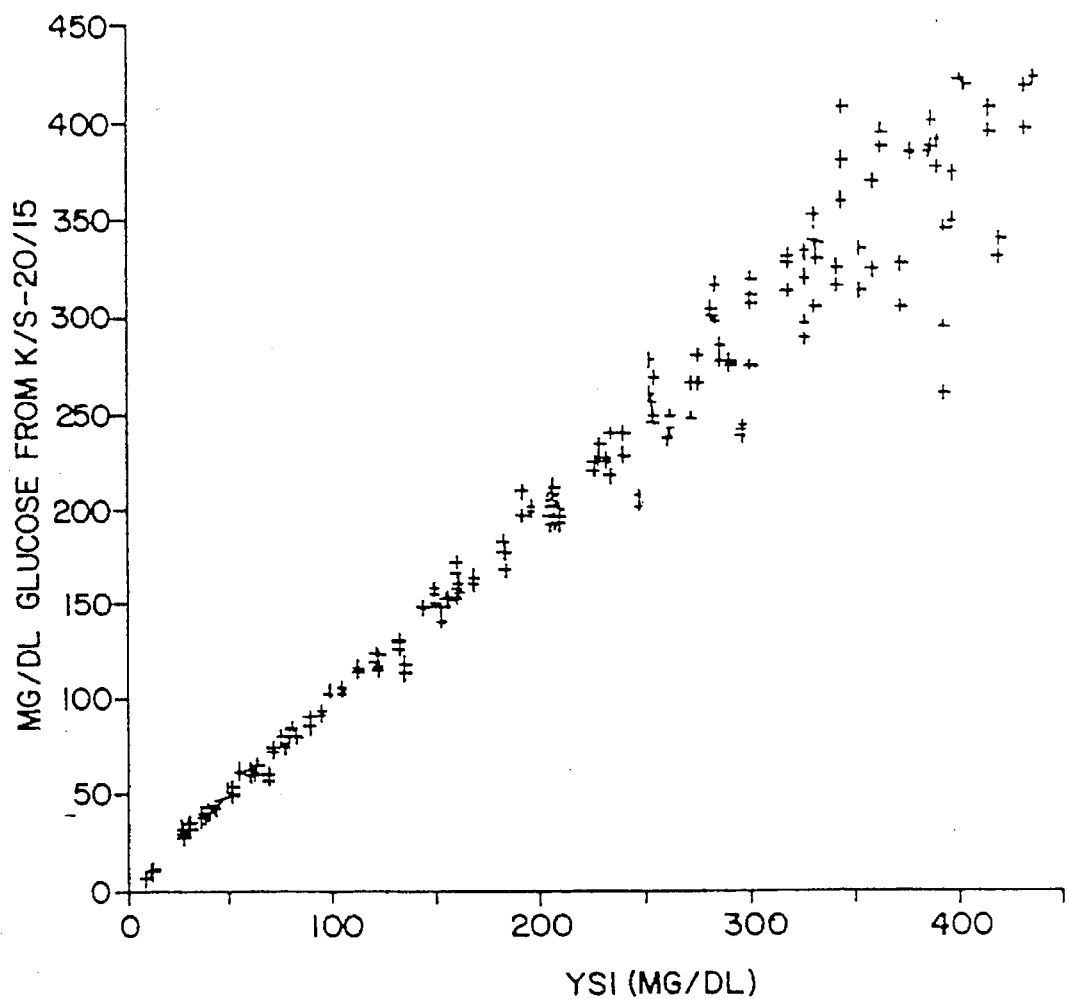
Figure 7B:
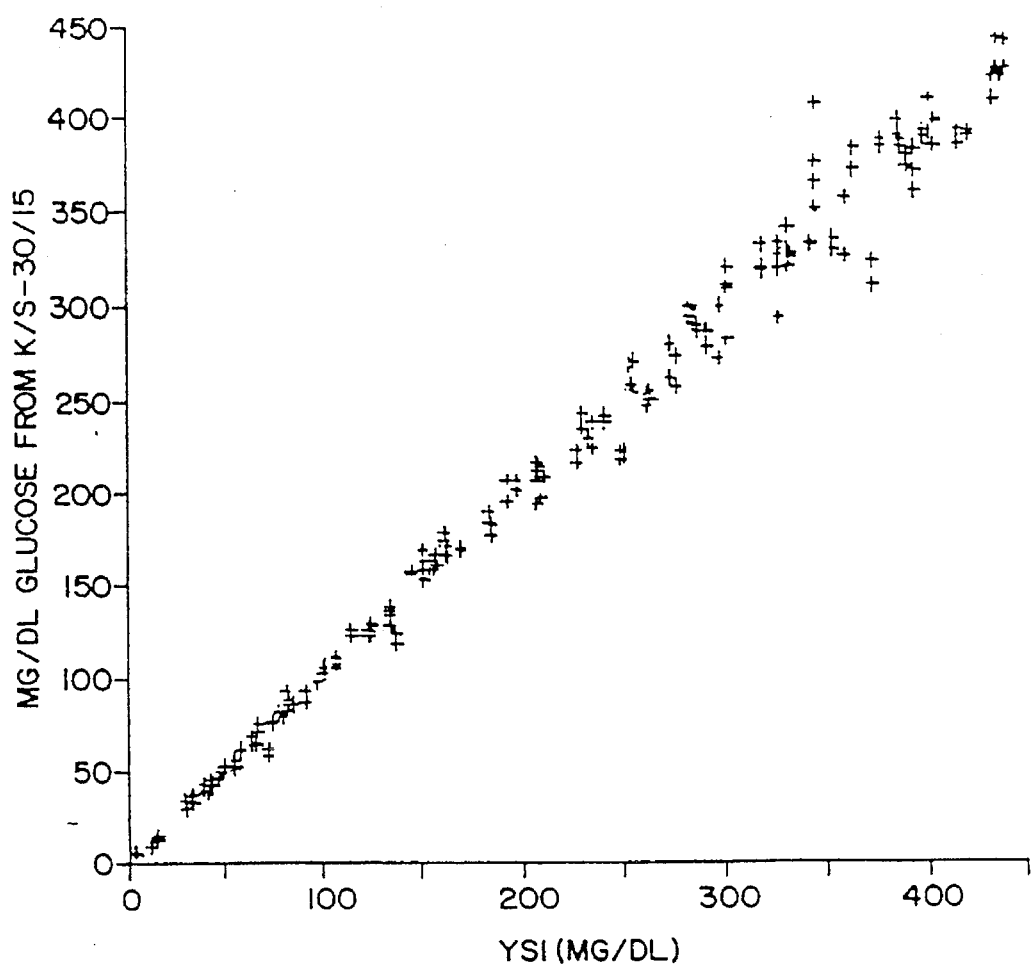
Figure 7D:
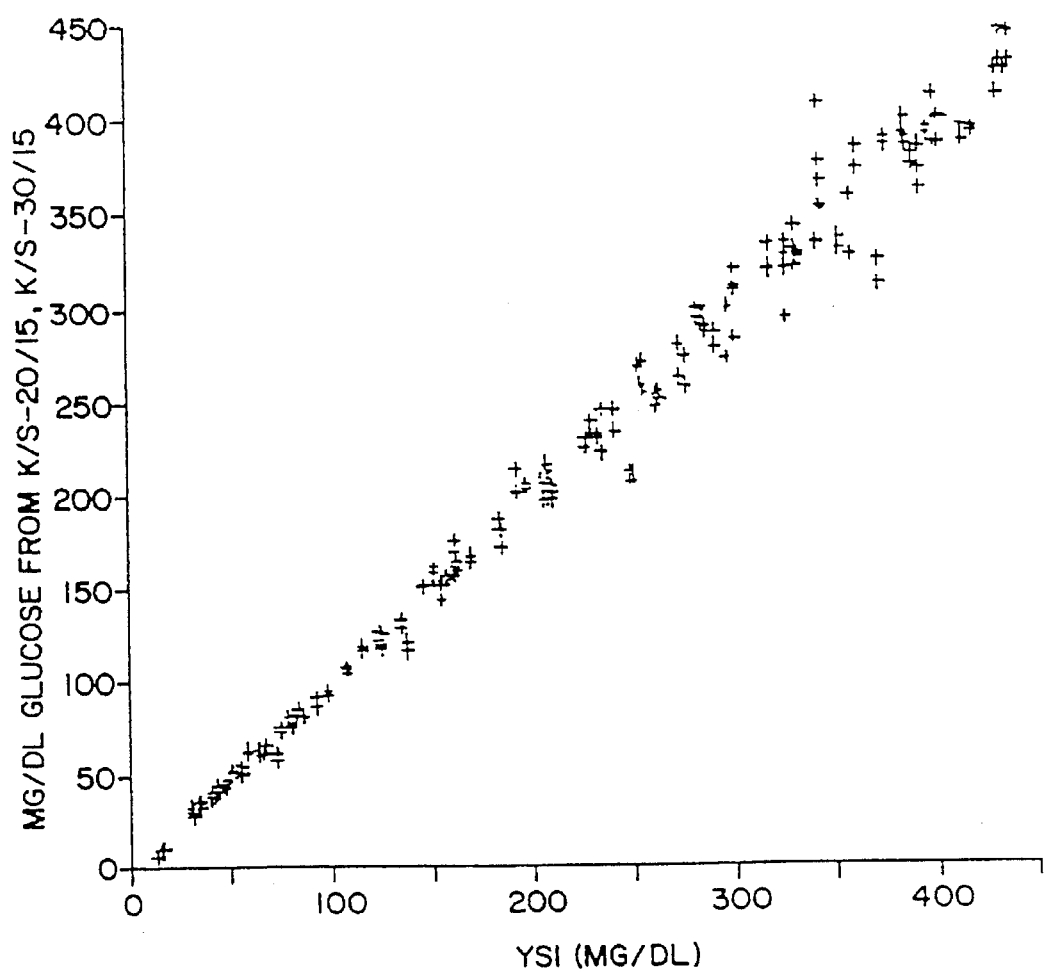

Response curves were constructed for the appropriate equation (see Tables 1 and 2). These MPX glucose values were then plotted vs. the YSI values to give scattergrams, as seen in FIGS. 6a and 6b for the Single Wavelength System, and FIGS. 7a through 7d for the Dual Wavelength System.

Comparison of MPX Systems:

For both the 20-second and 30-second measurement times there is visually more scatter in the single-wavelength scattergrams than the dual-wavelength scattergrams. The 20-second reading becomes very scattered above 250 mg/dl but the 30-second measurement does not have wide scatter until the glucose level is greater than 500 mg/dl.

These scattergrams were quantitated by determining the deviations from YSI at various glucose ranges. The following results were obtained.

TABLE 6

Accuracy of MPX System from Recovery Data

| MPX Wavelength | Measurement Time (sec.) | *S.D. (mg/dl) | C.V. for Range** (%) 0–50 | 50–250 | 250–450 |
|---|---|---|---|---|---|
| Single | 20 | ±5.6 | 7.2 | 14.5 | — |
| Single | 30 | ±6.9 | 7.1 | 8.8 | 10.2 |
| Dual | 20 | ±2.3 | 5.3 | 12.8 | — |
| Dual | 30 | ±2.19 | 5.5 | 5.8 | 8.4 |

\* = Standard Deviation
\*\* = These are inter-method covariances

Note that:
a. The dual wavelength system gave results that ranged 30% lower than the single wavelength system.
b. The single wavelength system, from 0–50 mg/dl, showed a Standard Deviation of ±6–7 mg/dl whereas the Standard Deviation for a dual wavelength measurement was only ±2.2 mg/dl.
c. The cutoff for a 30-second MPX measurement is 250 mg/dl. For the 50–250 mg/dl range both the 20- and 30-second measurements gave similar inter-method covariances (approximately 7% for single wavelength, 5.5% for dual wavelength). However, in the 250–450 mg/dl range inter-method covariances more than double for the 20-second reading to 14.5% for the single and 12.8% for the dual wavelength.
d. The 30-second reading was unusable above 450 mg/dl for both the single and dual wavelength measurement (covariances of 10.2% and 8.4%).

In conclusion, the two MPX systems gave optimum quantitation in the 0–450 mg/dl range.

1. MPX System—30 Second Dual Wavelength:

This dual wavelength system gave a 30-second measurement time with a 95% confidence limit (defined as the probability of a measurement being within ±2 Standard Deviation of the YSI reading) of 11.3% covariance for the range from 50–450 mg mg/dl (Table 7) and ±4.4 mg/dl (Standard Deviation) for 0–50 mg/dl.

2. MPX System—30/20 Second Dual Wavelength:

This dual wavelength system gave a 20-second measurement time in the 0–250 mg/dl range and a 30-second time for the 250–450 mg range. The 95% confidence limits are nearly identical to the MPX 30 Second Dual Wavelength system (Table 7), 11.1% covariance for 50–450 mg/dl and ±4.6 mg/dl (Standard Deviation) for 0–50 mg/dl.

TABLE 7

Comparison of 95% Confidence Limits for the MPX System, GlucoScan Plus and Accu-Chek bG**** Reagent Strips

| Measuring Range | MPX Single Wavelength | | MPX Dual Wavelength | |
|---|---|---|---|---|
| mg/dl | 20 sec. | 30 sec. | 20 sec. | 30 sec. |
| 0–50 | 11.2 mg/dl | 13.8 mg/dl | 4.6 mg/dl | 4.4 mg/dl |
| 50–250 | 14.4 | 14.2 | 10.6 | 11.0 |
| 250–450 | — | 17.6 | — | 11.6 |
| 77–405 | GlucoScan Plus (Drexler Clinical) | | | 15.9% |
| 77–405 | Accu-Chek bG (Drexler Clinical) | | | 10.7% |
| 50–450 | MPX System 20/30 Sec. Dual Hybrid | | | 11.1% |
| 50–450 | MPX System 30 Sec. Dual Wavelength | | | 11.3 |

****Confidence limits for MPX were from the YSI. The confidence limits for GlucoScan Plus and Accu-Chek bG were from the regression equation vs. YSI which eliminates bias due to small differences in calibration.

EXAMPLE III

Stability:

Most of the bench-scale work carried out in optimizing stability was completed using hand-dipped 0.8µ Posidyne™ membrane disks. The specific dye/enzyme formulation was set forth previously.

1. Room Temperature Stability: This study attempted to chart any change in response of the 0.8µ Posidyne™ membrane reagent stored at 18° C.–20° C. over silica gel desiccant. After 2.5 months there was no noticeable change as measured by the response of a room temperature sample vs. the response of a sample stored at 5° C. Each measurement represented a glucose range of 0–450 mg/dl.

2. Stability at 37° C.: Stability study using the same reagent as the room temperature study was carried out. The differences in glucose values of reagent stressed at 37° C. vs. room temperature reagent, for strips stressed with and without adhesive, was plotted over time. Although the data was noisy, due to the poor reproducibility of handmade strips, the stability was excellent for strips whether they were stressed with or without adhesive.

EXAMPLE IV

Sample Size:

The sample size requirements for the MPX System are demonstrated in Table 9.

TABLE 9

Effect of Sample Size on MPX System Measurements

| Sample Size (μl) | Dual Wavelength | | | | | Single Wavelength | | | | |
| --- | --- | --- | --- | --- | --- | --- | --- | --- | --- | --- |
| YSI = 56 | | | | | | | | | | |
| 3 | 41 | 50 | 39 | 31 | 40 | 31 | 42 | 30 | 19 | 30 |
| 4 | 44 | 49 | 49 | 49 | 48 | 41 | 45 | 44 | 45 | 44 |
| 5 | 54 | 48 | 49 | 51 | 50 | 50 | 49 | 48 | 49 | 49 |
| 10 | 48 | 48 | 50 | 47 | 48 | 54 | 53 | 56 | 55 | 54 |
| 20 | 49 | 49 | 49 | 50 | 49 | 55 | 57 | 58 | 60 | 58 |
| YSI = 360 | | | | | | | | | | |
| 3 | 301 | 260 | 276 | 286 | 280 | 274 | 232 | 244 | 260 | 252 |
| 4 | 383 | 378 | 367 | 341 | 367 | 361 | 356 | 342 | 318 | 344 |
| 5 | 398 | 402 | 382 | 370 | 388 | 378 | 387 | 366 | 351 | 370 |
| 10 | 364 | 362 | 378 | 368 | 368 | 356 | 358 | 379 | 369 | 366 |
| 20 | 375 | 370 | 380 | 378 | 376 | 380 | 382 | 389 | 385 | 384 |

3. Stability at 56° C.: Eight 5-day to 6-day stability studies were carried out using different preparations of a similar formulation on disk membrane (Table 8). For the low glucose test level (80–100 mg/dl) the average glucose value dropped upon stressing by 3.4% with the highest drop being 9.55%. At the high test level (280–320 mg/dl) the glucose reading declined by an average of 3.4%, the largest decline being 10.0%.

TABLE 8

Stability of pH = 4.0, .8μ Posidyne ™ Disk Reagent Formulation Stressed for 5 Days to 6 Days at 56° C.

| Sample No. | % Difference (56° C. vs. Room Temperature Sample) | |
| --- | --- | --- |
| | YSI (80–100 mg/dl) | YSI (280–320 mg/dl) |
| FJ22B | −6.25 | +5.4 |
| FJ27A | −4.0 | −5.14 |
| FJ28B | −2.4 | −5.3 |
| FJ30H | −9.55 | −10.0 |
| FJ31C | +4.43 | −1.24 |
| FJ36 | −3.2 | −8.5 |
| FJ48B* | −3.0 | 0.0 |
| GM48A* | −3.0 | −2.5 |
| Average of 8 | −3.4 | −3.4 |

*These two samples contained twice the normal concentration of enzyme and dye.

A study of the 56° C. stressing of this membrane over a 19-day period showed no major difference for strips stressed with or without adhesive. In both cases the 19-day decline in glucose value was less than 15% at low test levels (80–100 mg/dl) and also at 300 mg/dl.

Another 56° C. study using hand-dipped 0.8μ Posidyne™ membrane with twice the normal concentration of enzyme and dye was completed. Two separate preparations of the same formulation were made up and the stability measured over a 14-day period. The average results of the two studies were compared. Changes were within ±10% over the 14-day period at both the high and low glucose test level.

The volumes reported in the table were transferred to the reagent pad 10 shown in FIG. 1 using a micropiper. When blood from a finger stick is applied to a strip the total sample cannot be transferred. Therefore, the volumes reported here do not represent the total sample size needed to be squeezed from the finger for the analysis. A 3 μl sample is the minimum necessary completely cover the reagent pad circle. This does not provide enough sample to completely saturate the reagent pad and the MPX System, whether single or dual wavelength, gives low results. A 4 μl sample barely saturates the reagent pad, while a 5 μl sample is clearly adequate. A 10 μl sample is a large shiny drop and a 20 μl sample is a very large drop and is only likely to be used when blood from a pipet is used for sampling.

At the lower glucose concentration the single wavelength result has some dependence on sample size, which is completely eliminated using the dual wavelength measurement. Although this dependence with the single wavelength might be considered acceptable, it is clearly undesirable.

EXAMPLE V

Reproducibility:

Experimental measurements described above were always run in replicate, usually 2,3 or 4 determinations per data point. These sets have always shown close agreement even for samples with extreme hematocrits or extreme oxygen levels. covariances were well below 5%. It appears, therefore, that reproducibility is very good to excellent.

The subject invention provides for many commercially or have been described in the literature. The protocols are simple and require little technical skill and are relatively free of operator error. The assays can be carried out rapidly.

They use inexpensive and relatively harmless reagents, important considerations for materials employed in the home. The user obtains results which can be understood and used in conjunction with maintenance therapy. In addition, the reagents have long shelf lives, so that the results obtained will be reliable for long periods of time. The equipment is simple and reliable and substantially automatic.

All patents and other publications specifically identified in this specification are indicative of the level of skill of those of ordinary skill in the art to which this invention pertains and are herein individually incorporated by reference to the same extent as would occur if each reference were specifically and individually incorporated by reference.

The invention now being fully described, it will be apparent to one of ordinary skill in the art that many modifications and changes can be made thereto without departing from the spirit or scope of the invention as defined in the following claims.

What is claimed is:

1. A whole blood glucose test strip for measuring a concentration of glucose in an unmeasured whole blood sample which does not require removal of excess sample, said test strip being adapted for use in a reflectance reading apparatus which measures reflectance at about 635 nm and about 700 nm, said test strip comprising:

a handle having an aperture defined therein; and a porous, hydrophilic matrix disposed over said aperture such that one surface of the matrix is exposed to atmosphere adjacent to one side of the strip and the other surface of the matrix is exposed to atmosphere on the other side of said strip through said aperture, one of said surfaces being an upper sample receiving surface adapted to receive said whole blood sample on one side of the matrix and the second of said surfaces being a lower testing surface from which diffuse reflected light is measurable, said testing surface being opposite to said sample receiving surface, said matrix allowing at least a portion of said blood sample to penetrate through the matrix from said sample receiving surface to said testing surface, allowing blood color of said blood sample to be observed from the testing surface, and filtering out red blood cells such that they do not reach the testing surface, said matrix comprising reagent means for chemically reacting with glucose to create a change in reflectance which change is indicative of the concentration of glucose present in said sample, whereby upon application of said unmeasured whole blood sample to the sample receiving surface, said sample will penetrate through the matrix sufficiently to allow said change in reflectance to be determined from said testing surface.

2. The test strip of claim 1 wherein said matrix is a single layer.

3. The test strip of claim 1 wherein said matrix further comprises ethylenediamine tetraacetic acid.

4. The test strip of claim 1 wherein said matrix further comprises polypeptide.

5. The test strip of claim 1 wherein said matrix further comprises citrate buffer.

6. The test strip of claim 1 wherein said matrix further comprises polymethylvinyl ether/maleic anhydride.

7. The test strip of claim 1 wherein said matrix further comprises medium viscosity copolymer of polymethylvinyl ether/maleic anhydride.

8. The test strip of claim 1 wherein said matrix further comprises ethylenediamine tetraacetic acid, polypeptide, citrate buffer, and polymethylvinyl ether/maleic anhydride.

9. The test strip of claim 1 wherein said matrix comprises polyamide.

10. The test strip of claim 1 wherein said matrix comprises a microfiltration membrane made from nylon cast on a core of non-woven polyester fibers.

11. The test strip of claim 1 wherein the surface of said matrix is positively charged.

12. The test strip of claim 1 wherein the surface of said matrix is functionalized with quaternary amine groups.

13. The test strip of claim 1 wherein the surface of said matrix is negatively charged.

14. The test strip of claim 1 wherein the surface of said matrix is functionalized with carboxyl groups.

15. The test strip of claim 1 wherein said matrix comprises unfunctionalized nylon.

16. The test strip of claim 1 wherein said matrix has an average pore size of from about 0.2 to 2.0 µm.

17. The test strip of claim 1 wherein said matrix has an average pore size of from about 0.5 to 1.2 µm.

18. The test strip of claim 1 wherein said matrix has an average pore size of from about 0.6 to 1.0 µm.

19. The test strip of claim 1 wherein said matrix has an average pore size of about 0.8 µm.

20. The test strip of claim 1 wherein said matrix has a thickness of less than about 0.5 mm.

21. The test strip of claim 1 wherein said matrix has a thickness of from about 0.1 mm to about 0.3 mm.

22. The test strip of claim 1 wherein said matrix has a thickness of from about 0.1 mm to about 0.2 mm.

23. The test strip of claim 1 wherein said reagent means comprises dye precursors which form a dye couple which develops color in the presence of oxygen.

24. The test strip of claim 23 wherein said dye precursors comprise 3-dimethylaminobenzoic acid and 3-methyl-2-benzothiazolinone hydrazone hydrochloride.

25. The test strip of claim 1 wherein said reagent means comprises dye precursors comprising 4-aminoantipyrene and chromotropic acid.

* * * * *